United States Patent
Park et al.

(10) Patent No.: US 9,539,574 B2
(45) Date of Patent: Jan. 10, 2017

(54) ANALYTE INJECTION SYSTEM

(75) Inventors: Charles Park, Mountain View, CA (US); Persefoni Kechagia, Williamsville, NY (US); Michael Spaid, Mountain View, CA (US); Morten Jensen, San Francisco, CA (US); Irina G. Kazakova, Los Gatos, CA (US); Josh Molho, Oakland, CA (US)

(73) Assignee: Caliper Life Sciences, Inc., Hopkinton, MA (US)

( * ) Notice: Subject to any disclaimer, the term of this patent is extended or adjusted under 35 U.S.C. 154(b) by 690 days.

(21) Appl. No.: 12/902,006

(22) Filed: Oct. 11, 2010

(65) Prior Publication Data

US 2011/0024296 A1 Feb. 3, 2011

Related U.S. Application Data

(62) Division of application No. 10/936,159, filed on Sep. 7, 2004, now abandoned.

(60) Provisional application No. 60/500,387, filed on Sep. 5, 2003, provisional application No. 60/518,169, filed on Nov. 7, 2003.

(51) Int. Cl.
*G01N 27/447* (2006.01)
*B01L 3/00* (2006.01)

(52) U.S. Cl.
CPC .... *B01L 3/502753* (2013.01); *B01L 3/502746* (2013.01); *G01N 27/44743* (2013.01); *G01N 27/44773* (2013.01); *G01N 27/44791* (2013.01); *B01L 3/502715* (2013.01); *B01L 2200/0673* (2013.01); *B01L 2200/16* (2013.01); *B01L 2300/0816* (2013.01); *B01L 2400/0415* (2013.01); *B01L 2400/084* (2013.01)

(58) Field of Classification Search
CPC .................................................... G01N 27/447
USPC ............................................................ 204/451
See application file for complete search history.

(56) References Cited

U.S. PATENT DOCUMENTS

| | | | |
|---|---|---|---|
| 5,194,133 A | 3/1993 | Clark et al. | |
| 5,858,195 A * | 1/1999 | Ramsey | 204/601 |
| 5,958,791 A | 9/1999 | Roberts et al. | |
| 6,176,991 B1 * | 1/2001 | Nordman | 204/601 |
| 6,270,641 B1 * | 8/2001 | Griffiths et al. | 204/451 |
| 6,284,113 B1 | 9/2001 | Bjornson et al. | |
| 2002/0008029 A1 * | 1/2002 | Williams et al. | 204/453 |

FOREIGN PATENT DOCUMENTS

| | | |
|---|---|---|
| DE | 19927535 A1 | 1/2001 |
| WO | 99/24828 A1 | 5/1999 |

OTHER PUBLICATIONS

Benedikt Grass et al., "A new PMMA-microchip device for isotachophoresis with integrated conductivity detector," Sensors and Actuators B vol. 72 (2001) pp. 249-258, Elsevier.

* cited by examiner

*Primary Examiner* — Jennifer Michener
*Assistant Examiner* — Dustin Q Dam
(74) *Attorney, Agent, or Firm* — Cardinal Law Group

(57) ABSTRACT

This invention provides methods and systems for injection of analytes into a separation channel for resolution and detection. Samples can be preconditioned and concentrated by isotachophoresis (ITP) before the injection is triggered by a detected voltage event. Separation of analytes from other sample constituents can be enhanced using skewing channel ITP.

21 Claims, 18 Drawing Sheets

ANALYTE INJECTION SYSTEM

CROSS-REFERENCE TO RELATED APPLICATIONS

This application is a divisional of U.S. patent application Ser. No. 10/936,159, filed Sep. 7, 2004, and claims the benefit of U.S. Provisional Application No. 60/500,387, filed Sep. 5, 2003, and U.S. Provisional Application No. 60/518,169, filed Nov. 7, 2003.

BACKGROUND OF THE INVENTION

Field of the Invention

The present invention is in the field of analytical electrophoresis systems and methods. The invention can include high resolution and highly sensitive Isotachophoresis (ITP) and capillary electrophoresis (CE) assays.

Description of the Related Art

Electrophoresis is generally the movement of charged molecules in an electric field. Analytical methods based on electrophoresis have found broad utility, especially in the fields of protein and nucleic acid analyses. Samples having charged analyte molecules of interest can be placed in a selective media, such as size exclusion media, ion exchange media, or media having a pH gradient, where they can differentially migrate for high resolution from other sample molecules. The separated molecules can be detected for identification and quantitation.

Capillary and microfluidic scale electrophoretic separations are particularly popular for analyses requiring low sample volumes or high throughput. For example, chips of plastic or glass substrate can be fabricated with microscale loading channels, separation channels and detection channels. Samples can be transferred from microwell plates through a robotically manipulated sample collection tube to the loading channel. An electric potential can induce movement of sample constituents through selective media in the separation channel for sequential detection as the constituents elute into the detection channel from the separation channel. The microscale dimensions of the assay system can provide rapid analyses using microscale, or nanoscale, sample volumes. However, resolution or sensitivity may not be adequate for complex samples or dilute samples.

One approach to enhancing the resolution and sensitivity of capillary electrophoresis (CE) methods has been to pre-resolve and pre-concentrate the sample using Isotachophoresis (ITP) before CE separations. In ITP, the sample is loaded into a channel between a leading electrolyte (LE) having an electrophoretic mobility greater than the sample and a trailing electrolyte (TE) having electrophoretic mobility less than the sample. Under the influence of an electric field, analytes of interest can migrate through the sample bolus to accumulate at the interface with the LE and/or TE solutions. In this way, the analytes of interest can be separated from certain other constituents of the sample and concentrate to more detectable levels. Samples can thus be concentrated and desalted to provide improved injection material for further capillary electrophoresis separations resulting in highly sensitive detections with high resolution. For example, in "Tandem Isotachophoresis-Zone Electrophoresis via Base-Mediated Destacking for Increased Detection Sensitivity in Microfluidic Systems", by Vreeland, et al., Anal. Chem. (2003) ASAP Article, sample concentrated by ITP is further resolved and detected by capillary zone electrophoresis (CZE). In Vreeland, the sample is subjected to ITP between a TE and an LE having electrophoretic mobilities controlled by the pH of Tris buffers. While ITP concentration of analytes progresses, hydroxyl ions (—OH) are formed by hydrolysis at the cathode end of the separation channel. Migration of the hydroxyl ions through the separation channel eventually neutralizes the Tris buffers to remove the mobility differences between the LE and TE solutions. The Tris neutralization converts the ITP separation media into a CZE separation media. The analytes can than be separated with higher sensitivity and resolution than for standard CZE of the same sample due to the effective sample volume reduction and concentration of analytes resulting from the ITP assay step. The Vreeland method is limited to pH based ITP of compatible samples, can be time consuming due to the neutralization step, and can be inconsistent due to variations in buffer preparation or hydroxyl ion generation.

In another scheme to combine ITP with CE, analytes of interest migrate in ITP mode until they reach an intersection with a CE separation channel before switching the electric field to the separation channel for capillary electrophoresis separation of the analytes. For example, in "Sample Preconcentration by Isotachophoresis in Microfluidic Devices", by Wainright, et al., J. Chromat. A979 (2002), pp. 69-80, samples are pre-concentrated in a ITP channel until they reach an intersection with a CE channel. The intersection is monitored microscopically by a photomultiplier tube (PMT) receiving light through a confocal lens focused on the intersection. Analytes entering the intersection can be detected, e.g., by fluorescence or light absorption, and the electric field manually switched to inject the analytes into the CE channel. Problems exist, however, in that the manual switching can be inconsistent, some analytes may not be detectable using a PMT, and PMT detection at the microscale can be cumbersome and expensive.

In view of the above, a need exists for increased sensitivity, consistency, and resolution of capillary and microscale electrophoresis methods. It would be desirable to have systems that can automatically and consistently switch between electrophoretic modes. The present invention provides these and other features that will be apparent upon review of the following.

SUMMARY OF THE INVENTION

The present invention provides, e.g., systems and methods to consistently inject analytes into separation media based on a triggering voltage event. The analytes can be preconditioned and concentrated in a channel by isotachophoresis (ITP) stacking, followed by application of the stacked analytes to a separation channel segment, when a voltage event is detected in the channel.

The methods of the invention can provide highly repeatable analytical results with high sensitivity, speed and resolution. The method can include, e.g., analyte injection by stacking one or more analytes in a stacking channel segment, detecting a voltage potential in the channel, and applying the stacked analyte into a separation channel segment by applying an electric field or a pressure differential along the separation channel segment when a selected voltage event is detected. The channel can be a microscale channel, e.g., with intersecting or common channel segments making up a loading channel segment, a stacking channel segment and/or a separation channel segment.

Stacking of analytes can take place in a stacking channel segment wherein analytes of interest can be sandwiched between buffers selected to focus the analytes into a concentrated band during ITP. Typical injected analytes include, e.g., proteins, nucleic acids, carbohydrates, glycoproteins, ions, and/or the like. The stacking channel segment can have a trailing electrolyte and/or a leading electrolyte which have different mobilities. For example, the leading electrolyte can have a faster mobility under the influence of an electric field than the trailing electrolyte or analytes of interest. In many embodiments, the trailing electrolyte and the leading electrolyte can differ in pH, viscosity, conductivity, size exclusion, ionic strength, ion composition, temperature, and/or other parameters that can affect relative migration of the electrolytes. The trailing electrolyte can be adjusted to have a mobility less than analytes so that the analytes accumulate at the trailing interface during ITP. Optionally, the leading electrolyte can be adjusted to have a mobility greater than the one or more analytes so that they can accumulate at the leading interface during ITP separations. By narrowly adjusting the migration rates of trailing and leading electrolytes, analytes can be focused between the leading and trailing electrolytes while sample constituents not of interest migrate to other zones of the stacking channel segment. That is, the trailing electrolyte can be adjusted to have a mobility greater than one or more sample constituents not of interest, or the leading electrolyte can be adjusted to have a mobility less than one or more sample constituents not of interest so that they are not focused with the analyte of interest between the electrolytes.

When the channel of the analyte injection method includes separate stacking and separation channel segments, switching from the stacking channel to the separation channel segment can be by switching the electric field from the stacking channel segment to the separation channel segment, e.g., when the stacked analyte enters an intersection of the stacking and separation channel segments. For example, applying an electric field to the separation channel segment can include switching from a substantial lack of current in the separation channel segment while an electric current flows in the stacking channel segment to an electric current in the separation channel segment while electric current in the stacking channel segment is shut off. Shutting off (substantial lack) of current in the channel segments can be by application of a float voltage to prevent current flow in the channel segment or simply by provision of a high resistance in the channel segment (e.g., allowing no significant electric current outlet from the channel segment). Optionally, switching can be by exerting a pressure differential across the separation channel segment.

The separation channel segment in the injection methods can resolve analytes from other analytes or sample constituents. Such resolution can allow the analytes of interest to be identified or quantitated. Separation channel segments can have selective conditions or separation media to affect migration of analytes and sample constituents. For example, the separation channel can contain a pH gradient, size selective media, ion exchange media, a viscosity enhancing media, hydrophobic media, and/or the like.

Analytes resolved in separation channel segments can be detected for identification and/or quantitation. Detectors can be focused to monitor analytes in the separation channel segment or to detect analytes as they elute from the separation channel segment. Detecting analytes can be by monitoring parameters associated with the analytes, such as, e.g., conductivity, fluorescence, light absorbance, refractive index, and/or the like.

Sample solutions can be loaded to channels of the methods by a variety of techniques, e.g., to provide adequate sensitivity and speed. For example, when the loading channel does not hold enough sample analyte for the desired detection, multiple samples can be consecutively loaded and stacked before fusion of multiple stacks to provide an enhanced concentration of analyte in a small volume. Stacking two or more samples of the analytes can proceed by, e.g.: loading a first sample into a loading channel; applying an electric field across the sample, thereby stacking the sample; loading a second sample into the loading channel; and applying an electric field across the stacked sample and the second sample to stack the second sample and cause the two stacked samples to become focused together between trailing and leading electrolytes. The multiple stacking technique can be facilitated by flowing the stacked first sample towards the loading channel to clear excess electrolyte and depleted sample solution before loading the second sample. Another way to concentrate sample analytes can be, e.g., by loading samples of the analytes in a loading channel comprising a cross-section greater than a stacking channel segment cross-section so that analytes from a large sample volume do not have to migrate as far to accumulate at a trailing or leading electrolyte interface.

Spacer electrolytes, having migration rates intermediate to the trailing electrolyte and the leading electrolyte, can be loaded between samples and/or stacked analytes to resolve the sample into two or more analytes of interest. In one embodiment, stacking comprises loading one or more spacer electrolytes having a mobility greater than the trailing electrolyte and less than the leading electrolyte between two or more analyte sample segments. In another embodiment, one or more of the two or more analyte sample segments is a previously stacked sample analyte, and the spacer electrolyte is inserted during a multi-stacking load procedure. The spacer electrolytes can be adjusted to provide a mobility between mobilities of two or more of the analytes in order to resolve the analytes in ITP. Such spacer electrolyte adjustments can be made by selecting an appropriate electrolyte pH, spacer electrolyte constituents, spacer electrolyte viscosity, spacer electrolyte conductivity, and/or the like.

In some injection methods, electrolytes can be intelligently formulated to provide ITP resolution of analytes for injection. For example, if the pK of an analyte is determined, e.g., from experiments or calculations, leading and trailing electrolytes can be adjusted to pH values bracketing the pK so that analyte intruding into the leading electrolyte becomes less charged and less mobile, and/or analyte intruding into the trailing electrolyte becomes more charged and more mobile. Such adjustments can enhance the selectivity and concentration of ITP before injection of the stacked analyte.

The injection of stacked analyte into a separation channel segment can be triggered by detection of a selected voltage event. Voltages can be monitored at various locations in the channel and voltage events that precisely indicate preferred timing for injection can be determined. For example, detecting a voltage event can include monitoring a float voltage necessary to maintain a zero current flow (or other defined current flow) condition in the separation channel segment. Typical voltage events used to trigger the start of a separation can include, e.g., a voltage peak, a voltage trough, a predesignated voltage, relative voltage, or a rate of voltage change, (for example a zero slope observed at the top of a voltage profile). The switch to inject stacked analyte from ITP to the separation channel segment can be an automatic application of an electric field or pressure differential along the channel segment when the voltage event is detected.

Systems of the invention for injection of analytes can provide automated injection of stacked analytes for reliable, consistent, and sensitive analyses. Analyte injection systems can include, e.g., an analyte stacking in a channel, a voltage detector in electrical contact with the channel and in communication with a controller so that the controller can initiate a flow of electrical current in a separation segment of the channel, or a pressure differential along the channel segment, when a selected voltage event is detected by the voltage detector. Typically, the channel is a microscale channel having a loading channel segment, a stacking channel segment, and a separation channel segment.

A stacking channel segment in the system is usually configured for isotachophoresis procedures with a trailing electrolyte (TE) and/or a leading electrolyte (LE). The electrolytes can have different adjustable mobilities. For example, the electrolytes can have different pH values, viscosities, conductivities, size exclusion cut-offs, ionic strengths, ion compositions, or temperatures. Analytes for stacking in the channel can include molecules, such as proteins, nucleic acids, carbohydrates, glycoproteins, derivatized molecules, ions, and the like. Electrolytes can be tailored to selectively stack analytes of interest while rejecting other sample constituents. For example, the trailing electrolyte can be formulated to have a mobility less than the mobility of the analyte of interest and a mobility greater than a mobility of a sample constituent not of interest, so that the analyte accumulates on the front of the TE while the constituent falls away through the TE. The LE can be formulated to have a mobility greater than the mobility of the analyte of interest and a mobility less than a mobility of a sample constituent not of interest, so that the analyte can accumulate at the LE interface while the constituent migrates away in front of the LE interface.

The separation channel segment of the system can contain conditions or selective media to resolve analytes and constituents that have been stacked in the stacking column. For example, the separation column can include a pH gradient, size selective media, ion exchange media, hydrophobic media, viscosity enhancing media, and the like.

The controller can receive output from the voltage detector to initiate an injection when a selected voltage event is detected. The controller can be, e.g., a logic device or a system operator. In some embodiments, the injection event can be a switch from the stacking channel ITP electric field conditions to driving forces required to insert stacked analyte into a separation channel segment. For example, the injection can be a switch from the ITP current flow to substantial elimination of current in the stacking channel segment when the voltage event is detected, while a field or pressure is initiated in the separation channel segment.

The channel segments of the system can include a loading channel segment in fluid contact with the stacking channel segment. Various loading schemes can be employed to meet the demands of particular analyses. In one embodiment, the loading channel segment can have a cross-section greater than a stacking channel segment cross-section so that a larger volume of sample analyte can accumulate in the stacking channel segment in a shorter amount of time, i.e., the average analyte molecule has a shorter migration distance across a large cross-section loading channel segment than with a long loading channel segment of the same volume. In another aspect of loading, a first stacked analyte sample can be pulled back toward the loading channel segment before loading a second sample in a multiple stacking scheme to increase the analyte concentration and sensitivity of an assay. The "pull back" can be accomplished, e.g., by providing a pressure differential across the stacking channel segment to cause the first stacked sample to flow back toward the loading channel segment. Loading channel segments can be filled from, e.g., wells on a microfluidic chip, or by fluid handling systems, such as receiving samples from microarrays through a collector tube (sipper).

Spacer electrolytes can be used in the system, e.g., to enhance resolution between two or more analytes of interest. For example, a spacer electrolyte with a mobility between the mobilities of two or more analytes can be introduced between sample segments containing the analytes in the stacking channel segment. Analytes slower than the spacer electrolyte can partition behind the spacer while faster analytes can partition in front of the spacer. In an alternate embodiment, the sample analyte can be combined with spacer electrolytes, e.g., to partition into separate analyte zones, e.g., under the influence of transient or steady state conditions in ITP.

Systems of the invention can have voltage detectors in communication with controllers to detect and respond to voltage events in channels. Voltage detectors can detect voltages between two or more electric contacts across segments of channels, or between contacts at any location in the channel and a voltage reference, such as a ground. In some embodiments of the systems, the voltage detector monitors the voltage in the separation channel segment while stacking progresses. The voltage of the separation channel segment during stacking can be monitored at an intersection with the stacking channel segment or anywhere along the separation channel segment, e.g., when no substantial current flows in the separation channel segment, such as when a float voltage is being applied to the separation channel segment by a float voltage regulator, where there is no electrical outlet from one end of the channel segment, or where the channel segment has a controlling switch in the off position.

Controllers can automatically switch the system from stacking mode to separation mode on detection of a selected voltage event to inject stacked analytes into the separation channel segment. The voltage event can be, e.g., a voltage peak, a selected voltage, a voltage trough, a relative voltage, a rate of voltage change, and/or the like. The automatic switch can be, e.g., flowing of electrical current in the channel segment, a change in relative voltages across a channel segment, or application of a pressure differential along the channel segment to induce migration of the stacked analytes along the separation channel segment.

Analytes separated in the separation channel segments can be detected by analyte detectors of the system to identify and/or quantitate analytes of interest. Analyte detectors can be configured to monitor analytes in the separation channel segment, or analytes eluting from the separation channel segment. The analyte detector can comprise a fluorometer, a spectrophotometer, a refractometer, a conductivity meter, and/or the like.

The systems of the invention are well suited to microfluidic applications. For example, the loading channel segments, stacking channel segments, separation channel segments, detection chambers, and the like, can be incorporated into a microfluidic chip. The microscale dimensions of microfluidic devices are compatible with many systems of the invention. Microfluidic systems known in the art can provide voltages, pressures, fluid handling, communications, and detectors, etc., useful in practicing the systems of the present invention.

DETAILED DESCRIPTION

Figure 1A:
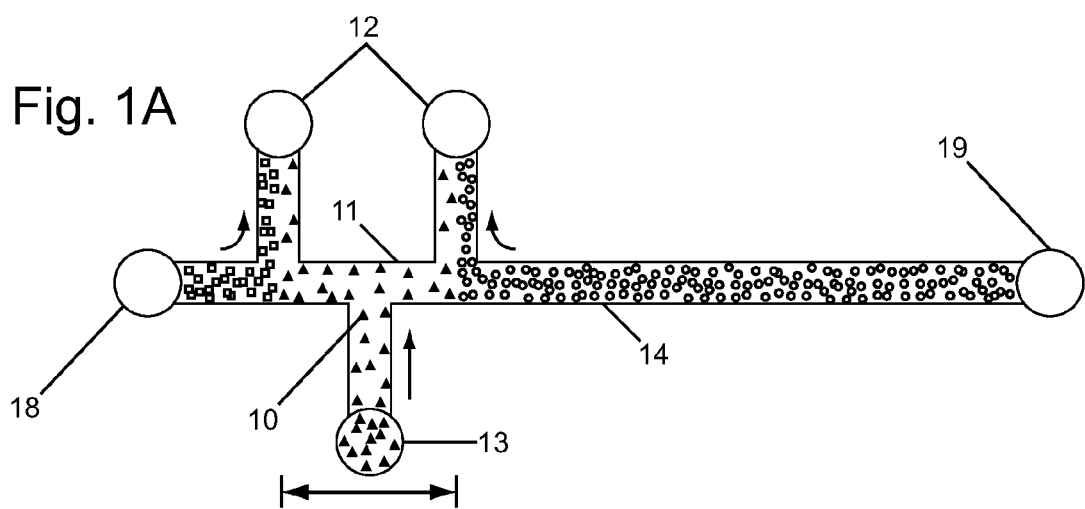
FIGS. 1A to 1C are schematic diagrams of an isotachophoresis system.

Unless otherwise defined herein or below in the remainder of the specification, all technical and scientific terms used herein have meanings commonly understood by those of ordinary skill in the art to which the present invention belongs.

Before describing the present invention in detail, it is to be understood that this invention is not limited to particular methods or systems, which can, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a constituent" can include a combination of two or more constituents; reference to "the analytes" can include one analyte, and the like.

Although many methods and materials similar, modified, or equivalent to those described herein can be used in the practice of the present invention without undue experimentation, the preferred materials and methods are described herein. In describing and claiming the present invention, the following terminology will be used in accordance with the definitions set out below.

The term "stacking," as used herein, refers to accumulation of one or more analytes at an interface with electrolytes having different mobilities in an electric field, e.g., during isotachophoresis. Stacking of analytes can also occur at other zones created, e.g., by migration modifying constituents present in the assay sample under transient (dynamic) or steady state conditions.

In "selective isotachophoresis" an analyte of interest with a known mobility can be separated from another sample constituent, such as, e.g., a sample constituent not of interest, e.g., by providing leading electrolyte and/or trailing electrolytes with mobilities intermediate to the mobilities of the analyte and sample constituent.

The term "analyte," as used herein, refers to constituents of a sample that are detected by an analyte detector. An "analyte of interest", as used herein, refers to an analyte for which detection and/or quantitation is desired in an assay.

The term "channel," as used herein, refers to a conduit for flowing and/or retention of fluids in methods and systems of the invention. Channels can be, e.g., tubes, columns, capillaries, microfluidic channels, and/or the like. A channel can include various channel segments, e.g., in separate sections of the channel, that share sections of the channel, and/or that intersect with other segments of the channel. Channel segments are generally functional sections of channel, such as, e.g., loading channel segments, stacking channel segments, and separation channel segments.

A "skewing channel" in the invention can be a channel segment that causes skewing of sample constituents flowing in the channel. For example, the internal surface topography of a skewing channel can cause bands or peaks to take on an oblique orientation relative to the channel axis while passing through the skewing channel.

The term "mobility," as used herein, refers to a rate of migration for charged molecules, such as analytes or electrolytes, in a solution under the influence of an electric field in a channel.

The term "float voltage," as used herein, refers to a voltage required in a channel segment to substantially prevent flow of an electric current through the segment or to establish a desired constant current in the segment.

The term "microscale," as used herein, refers to dimensions ranging from about 1000 μm to about 0.1 μm.

The invention relates to methods and systems for injection of analytes into separation channels. Stacking sample analytes can provide higher analyte concentrations in smaller injection volumes for electrophoretic separations with improved assay sensitivity and resolution. Sensitivity and separations can be improved, in many cases, by stacking analytes in skewing channels before injection. Automated timing of injections triggered by detection of voltage events can improve the consistency of results between assay runs.

Methods and systems of the invention can be used to separate, identify, and/or quantify analytes with a high level of sensitivity and resolution. Analytes of the invention can be, e.g., charged molecules, such as, e.g., proteins, nucleic acids, carbohydrates, glycoproteins, ions, derivatized molecules, and/or the like.

Methods of Analyte Injection

Methods of the invention can provide precise injection timing of stacked analyte into a separation channel for sensitive, repeatable, high resolution assays. Methods of the invention generally include, e.g., loading a sample to a loading channel segment before isotachophoresis (ITP) in a stacking channel segment, detecting a voltage event that indicates a stacked sample analyte is in position for injection, applying an electric field or pressure differential to apply the stacked sample analyte to a separation channel segment, and detecting separated analytes of interest. The ITP can include migration of the analytes through skewing channels. Detection signals can be evaluated to determine the presence or quantity of the analytes.

Stacking Analytes of Interest

Analytes of interest can be stacked into a volume less than the original analyte sample by isotachophoresis (ITP). For example, a sample bolus can be loaded between two different buffer systems in a channel and exposed to an electric current to create a steady state of solute zones migrating in order of decreasing mobility. In the steady state, the zones can adopt the same concentration and migrate along the channel at the same velocity as the leading electrolyte. Alternatively, a sample bolus can be loaded adjacent to an electrolyte and stacked in a dynamic (transient) condition at the interface for injection, e.g., without having reached a steady state equilibrium between ITP electrolytes.

Figure 1B:
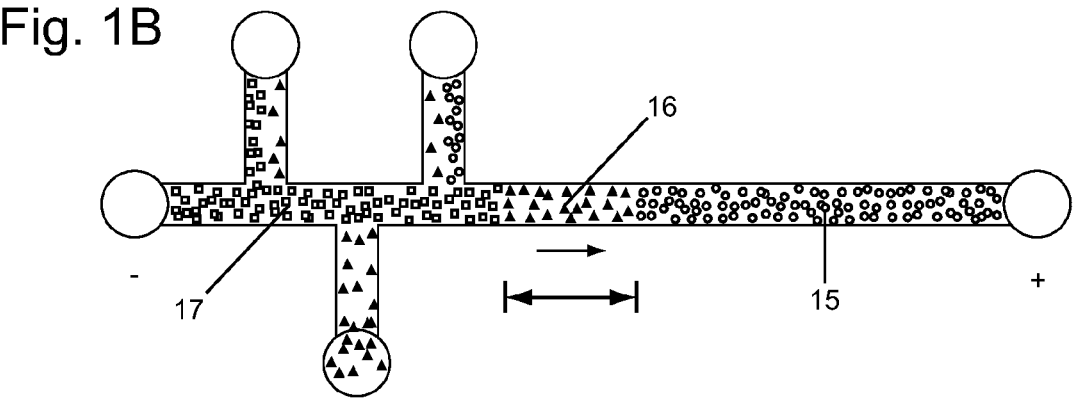
Figure 1C:
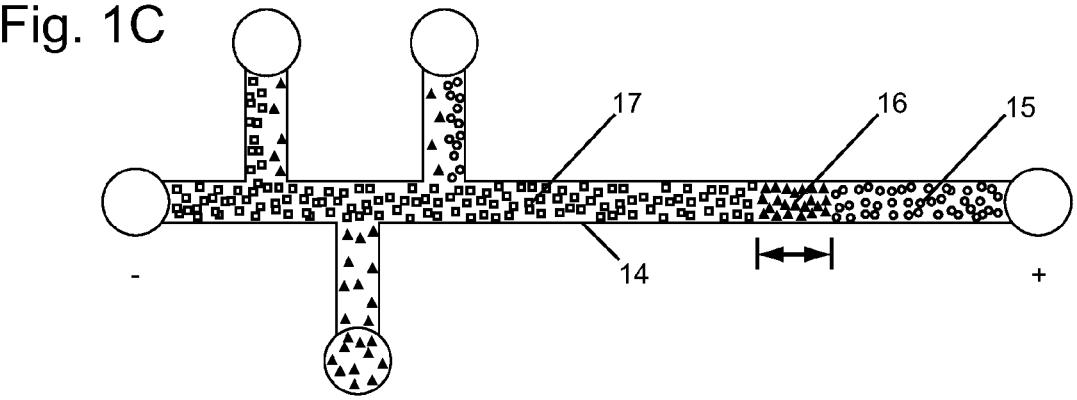

Stacking can be practiced, e.g., in channels of a microfluidic chip wherein a sample is loaded between channel regions of a trailing electrolyte and a leading electrolyte. As shown in FIG. 1A, analyte sample 10 can be loaded to loading channel segment 11 by a differential pressure between vacuum wells 12 and sample well 13. When an electric field is applied across stacking channel segment 14, current is carried by high mobility (e.g., high charge to mass ratio) leading electrolytes 15, intermediate mobility analytes 16, and low mobility trailing electrolyte 17, as shown in FIG. 1B. As ITP proceeds, a steady state can be established in which the volume of analyte 16 is reduced to the point where the concentration of charged analyte 16 is equivalent to the concentration leading electrolyte 15. In the steady state, the stacked analyte solution migrates along stacking channel segment 14 at the same rate as the leading and trailing electrolytes, as shown in FIG. 1C, with the electrolytes and charged analytes carrying the same amount of electric current per unit volume in the stacking channel segment. Factors, such as charge density and transient differential migration rates of the analytes and electrolytes, tend to focus the analytes and electrolytes into zones during ITP. Stacking channel segments of the invention can be any size including microscale channels having a dimension, such as width or depth, ranging from about 1000 µm to about 0.1 µm, or from about 100 µm to about 1 µm, or about 10 µm.

Figure 2A:
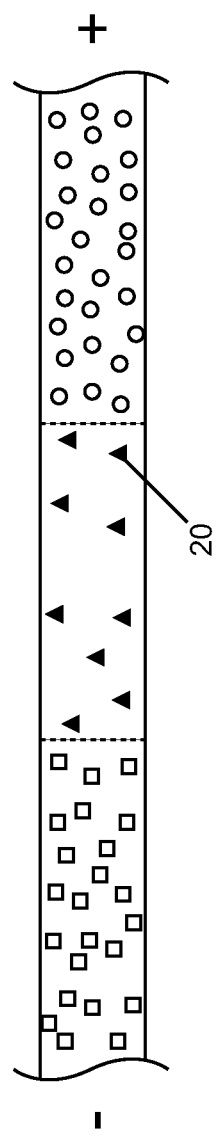
FIGS. 2A and 2B are schematic diagrams of transient ITP concentrating an analyte at an interface with a leading electrolyte.
Figure 2B:
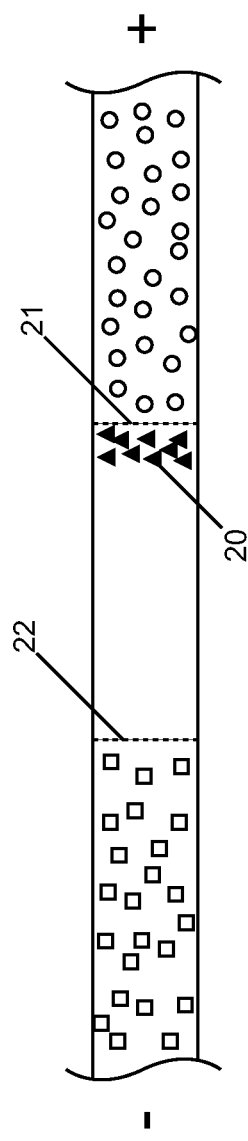

Stacking can also be practiced in a transient state. For example, as shown in FIG. 2A, initially dilute and dispersed analyte molecules 20 can accumulate, e.g., at leading electrolyte interface 21 as shown in FIG. 2B. This concentration of analyte at an interface can occur before establishment of steady state uniform analyte and electrolyte carrier concentrations. Optionally, an analyte can accumulate in a transient state, e.g., during initial application of an electric field in ITP, at trailing electrolyte interface 22. In other embodiments or transient ITP, analytes can become concentrated in zones other than interfaces of ITP electrolytes.

Figure 3A:
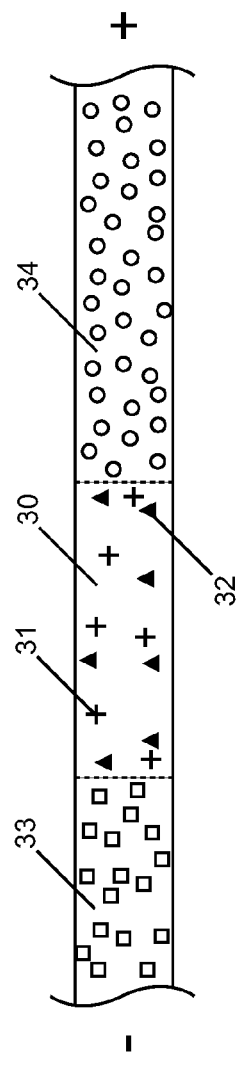
FIGS. 3A to 3C are schematic diagrams of transient ITP separation of analytes of interest and steady state ITP juxtaposition of the analytes.
Figure 3B:
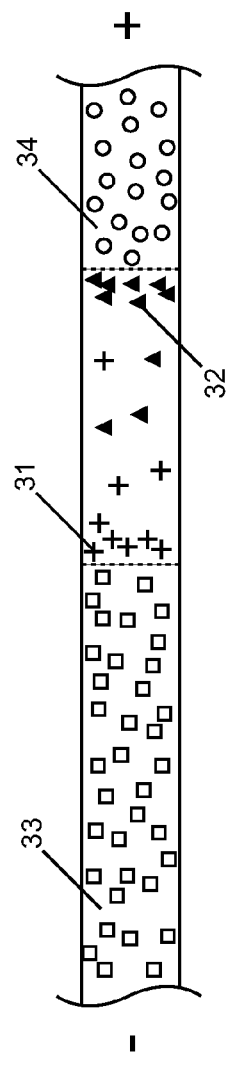
Figure 3C:
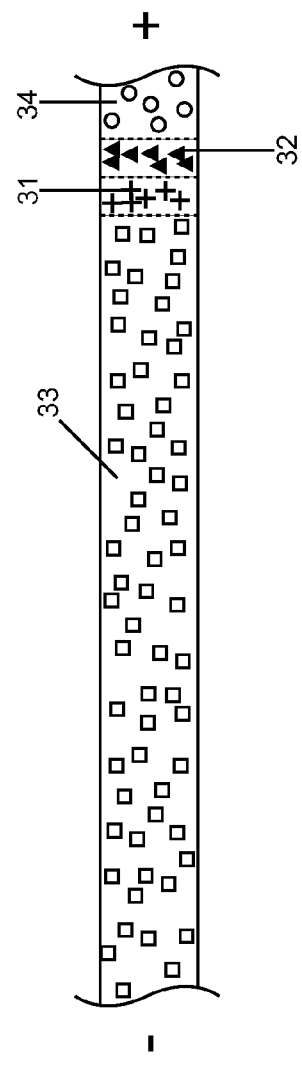

Multiple analytes of interest can accumulate in a steady state or transient state, e.g., at one or both of the electrolyte interfaces. For example, as shown in FIGS. 3A to 3C, sample solution 30 with first analyte of interest 31 and second analyte of interest 32 can be loaded between trailing electrolyte solution 33 and leading electrolyte solution 34. In the case where the first analyte has a slower mobility than the second analyte, but a faster mobility than the trailing electrolyte, the first analyte can accumulate at the interface with the trailing electrolyte in the presence of an electric field. Meanwhile, in the transient state, as shown in FIG. 3B, the second analyte, with somewhat higher mobility than the first analyte, can accumulate at the other end of the sample bolus along the interface with the faster mobility leading electrolyte. Such a situation can provide the opportunity for separate sequential or parallel application of the first and second analytes to one or more separation channel segments, as can be appreciated by those skilled in the art. Once a steady state has been established in the ITP, as shown in FIG. 3C, charged first and second analytes can become compressed into narrow adjacent bands, e.g., for application together for resolution in a separation channel segment.

Figure 4A:
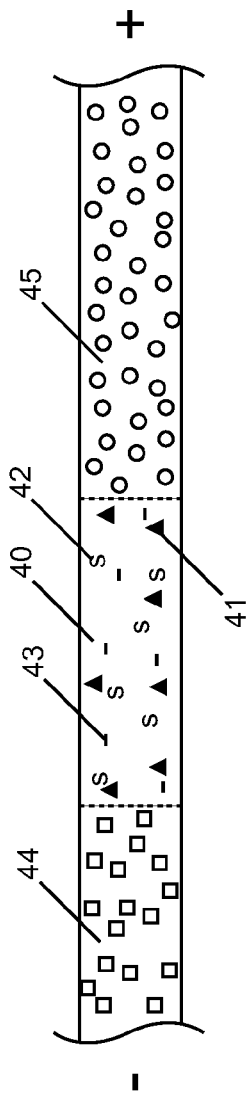
FIGS. 4A to 4C are schematic diagrams of selective removal of sample constituents during ITP.
Figure 4B:
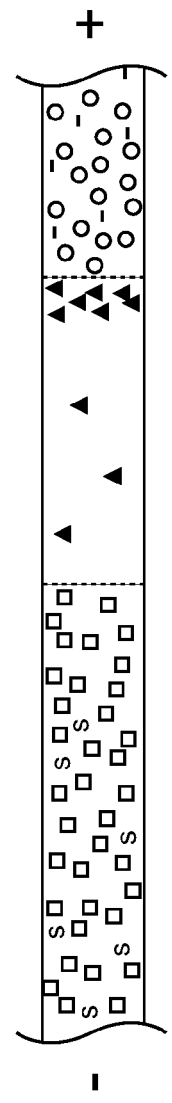
Figure 4C:
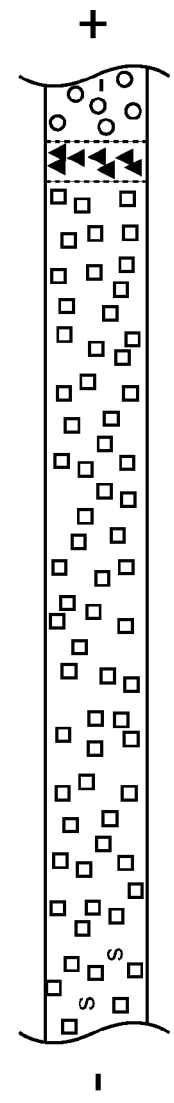

In methods of the invention, the mobilities of trailing electrolytes and leading electrolytes can be adjusted to provide selective pre-concentration of an analyte of interest while separating sample constituents not of interest from the analyte. For example, as shown in FIG. 4A, sample solution 40 containing analyte of interest 41, slow mobility sample constituent not of interest 42, and fast mobility sample constituent not of interest 43, can be loaded between trailing electrolyte 44 and leading electrolyte 45. When an electric field is applied to the channel, slow mobility sample constituents not of interest 42 can fall behind the trailing electrolytes while fast mobility sample constituent not of interest 43 can race ahead of the leading electrolytes, as shown in FIG. 4B. Continued ITP to a steady state can, e.g., further separate sample constituents not of interest from the analyte, as shown in FIG. 4C. Removal of sample constituents not of interest from analytes of interest can provide an improved injection material for separation in a separation channel segment. After samples have been pretreated by ITP to remove sample constituents not of interest, analyses of analytes of interest applied to a separation channel segment can have, e.g., reduced background noise, higher resolution due to lower injection volumes, more accurate quantitations due to better baselines and fewer overlapping peaks, etc.

Trailing electrolytes and leading electrolytes can be tailored, according to methods known in the art, by adjusting electrolyte mobilities to provide highly specific retention and stacking of analytes of interest, while sample constituents not of interest are removed. In one embodiment of the methods, the pH of electrolytes is selected to bracket the pK of an analyte of interest so that sample constituents not of interest having pKs outside the bracket will be removed in the ITP. The pK of the analytes of interest can be determined, e.g., empirically or based on the known molecular structure of the analytes. In other embodiments, the analyte of interest can be, e.g., closely bracketed between selected trailing and leading electrolyte compositions known to have slower and faster mobilities than the analyte. Many ions and buffers can be used in electrolytes to bracket analytes, such as, e.g., chloride, TAPS, MOPS, and HEPES. Optionally, the mobility of electrolytes and/or analytes can be modulated by adjusting the viscosity or size exclusion characteristics of the sample solution, trailing electrolyte solution, and/or leading electrolyte solution. In another option for adjusting the mobility of ITP solutions, mobility of analyte solutions and/or electrolyte solutions can be moderated, particularly during transient ITP migrations, by adjusting the concentration, ionic strength, or conductivity of the solutions. The temperature of solutions can be selected in still other options to adjust the mobility of analytes, electrolytes, or ITP solutions.

A variety of sample solution loading methods can benefit analyses in methods of the invention. Stacking channels can be loaded with single sample solution loads, with multiple sample solution loads, and with spacer electrolyte between sample solution loads, as described in detail below.

Figure 5A:
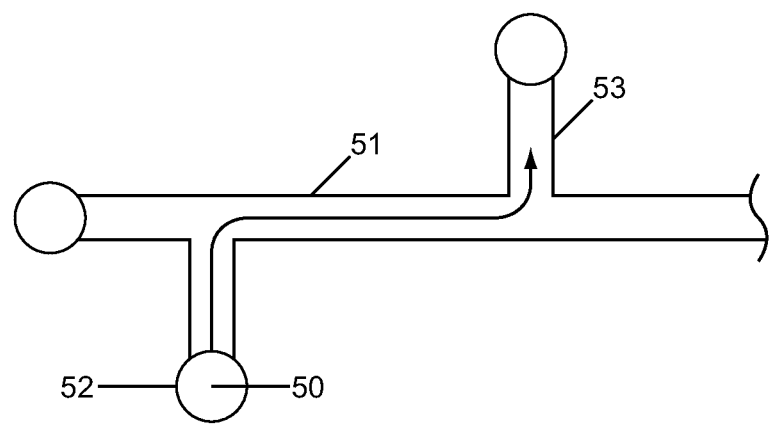
FIGS. 5A to 5C are schematic diagrams of exemplary sample solution loading techniques.
Figure 5B:
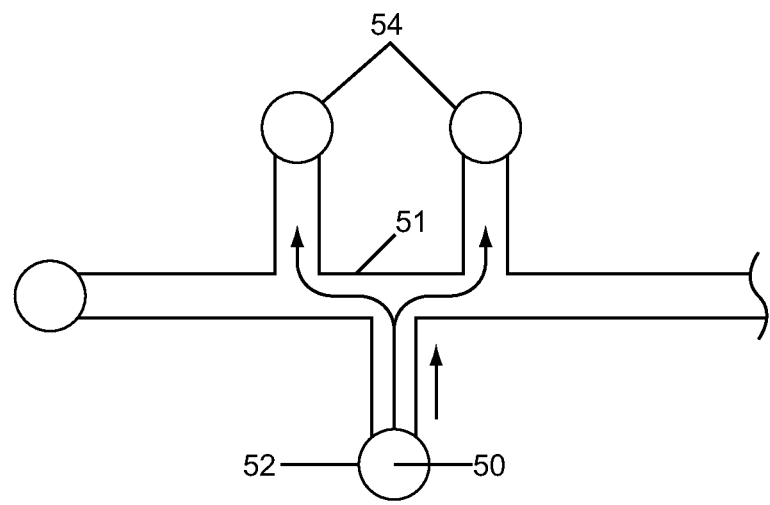
Figure 5C:
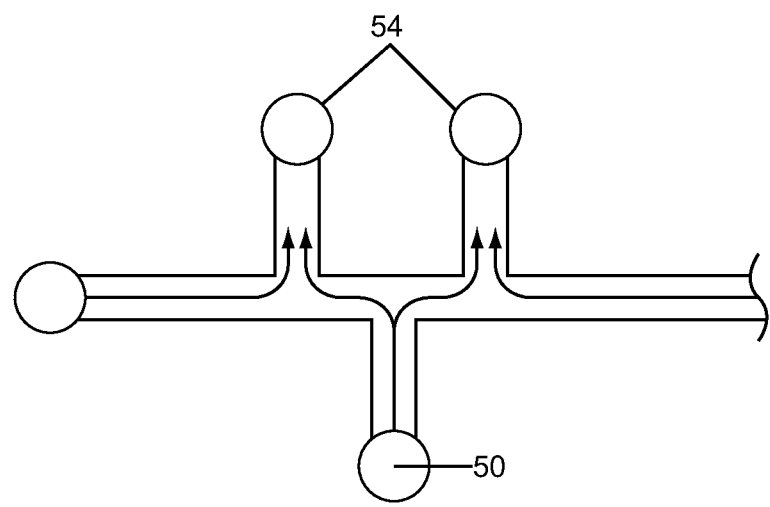

Single sample loads can be loaded to sample loading channel segments according to techniques known in the art, e.g., as shown in FIGS. 5A to 5C. Sample solution 50 can be applied to loading channel segment 51 using, e.g., electroosmotic flow (EOF) or a differential pressure to flow the sample solution from sample well 52 through the loading channel segment and out through waste channel 53 intersecting and offset along the loading channel segment, as shown in FIG. 5A. Alternately, Sample solution 50 can be loaded to branch into loading channel segment 51 under the influence of a differential pressure between sample well 52 and waste wells 54 as shown in FIG. 5B. In FIGS. 5A and 5B, the pressures in other wells with no flow must be adjusted to ensure zero flows. In another sample loading alternative, a relative vacuum at waste wells 54 can draw sample solution 50, the trailing electrolyte, and the leading electrolyte in a "pinching" flow, as shown in FIG. 5C, for precise and consistent definition of sample volumes.

Figure 6A:
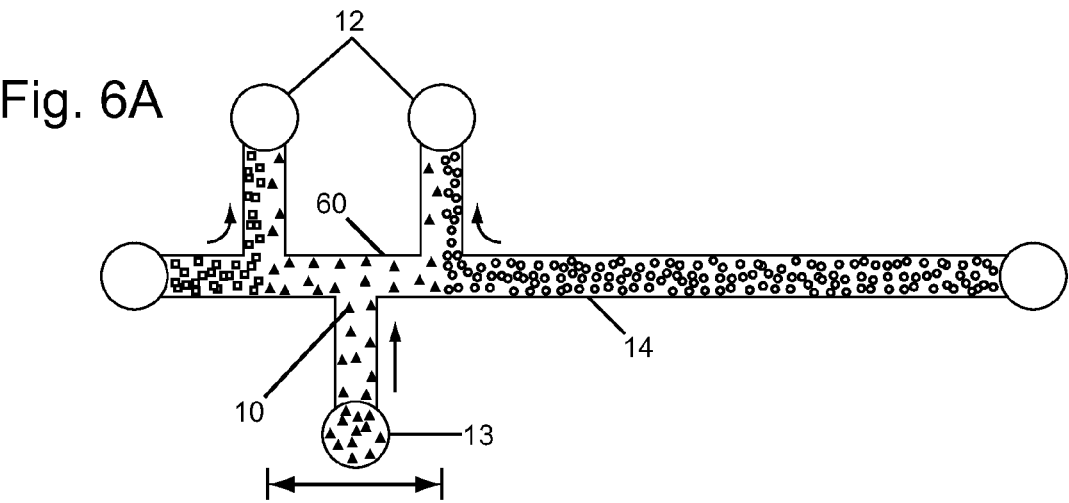
FIGS. 6A to 6E are sequential schematic diagrams describing a technique of stacking multiple loads of sample analytes.
Figure 6B:
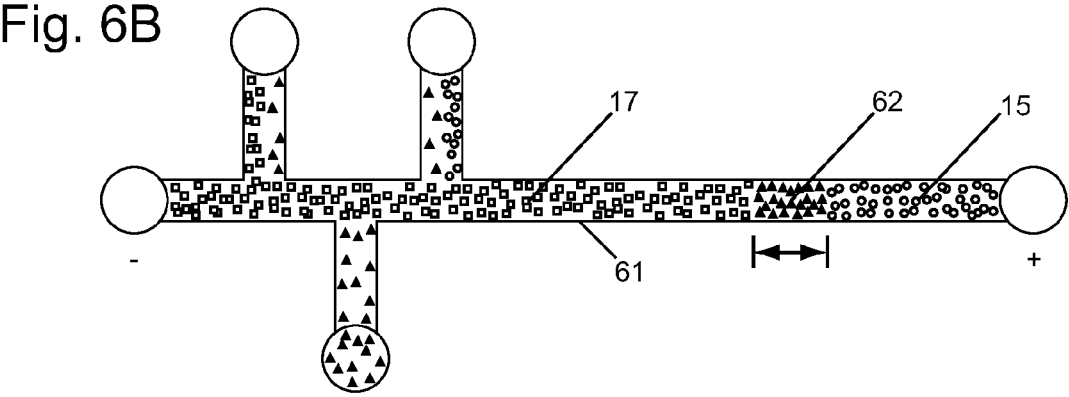
Figure 6C:
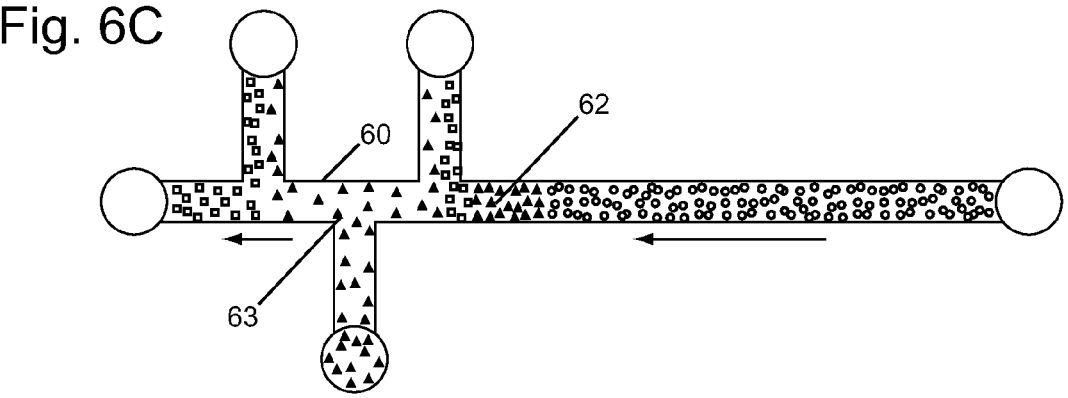
Figure 6D:
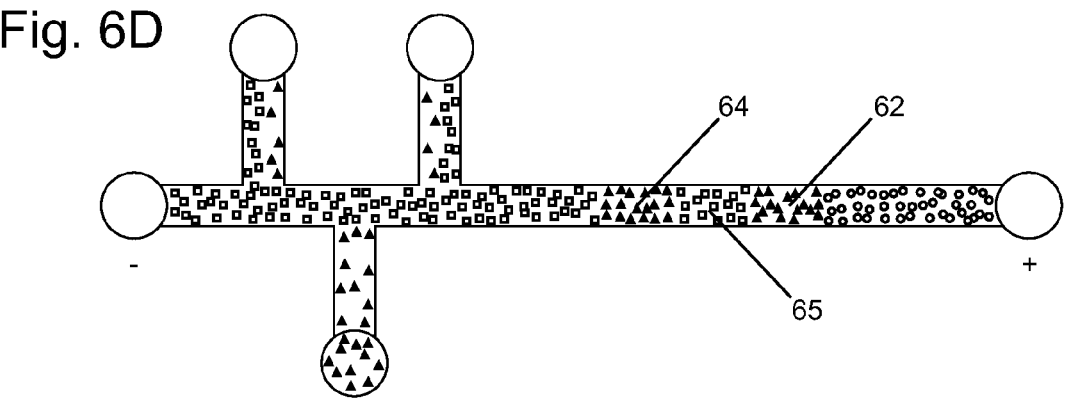
Figure 6E:
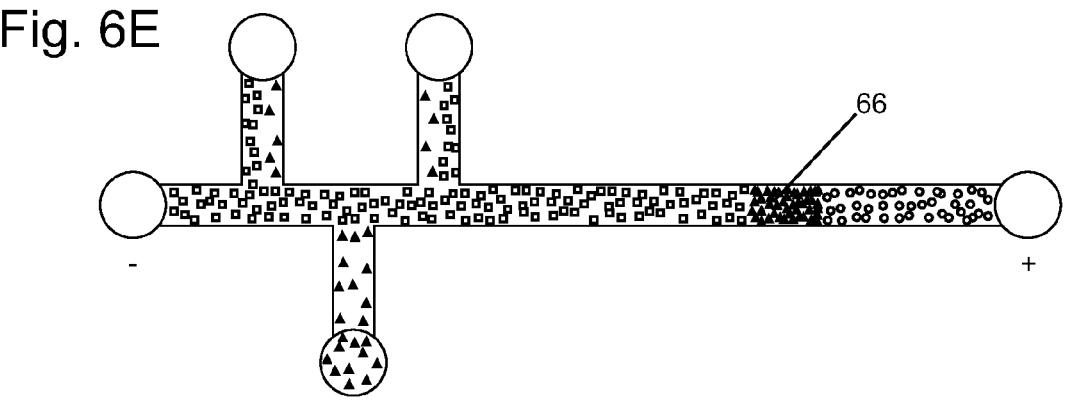

Additional amounts of sample solution can be loaded for ITP using a multiple stacking technique. A first sample can be loaded into loading channel segment 60 as shown in FIG. 6A. An electric field can be applied across stacking channel segment 61 to stack sample analytes 62, as shown in FIG. 6B. The stacked sample analytes 62 can be flowed back towards the loading channel segment and second load of sample solution 63 loaded adjacent to the first stacked analytes, as shown in FIG. 6C. An electric field can be applied across the stacking channel segment a second time to stack the second sample analytes 64, as shown in FIG. 6D. Separation zone 65, substantially composed of trailing buffer, can exist initially during the second stacking, but can dissipate as trailing electrolytes fall behind the second stack analytes in the electric field. Eventually, the first and second stacked analytes can combine under the influence of the electric field to form multiple stack 66 having, e.g., twice the amount of analytes as the first stack, as shown in FIG. 6E. The amount of analyte in the multiple stack can be further increased by additional rounds of stack pull back, sample loading, and stacking.

Figure 7A:
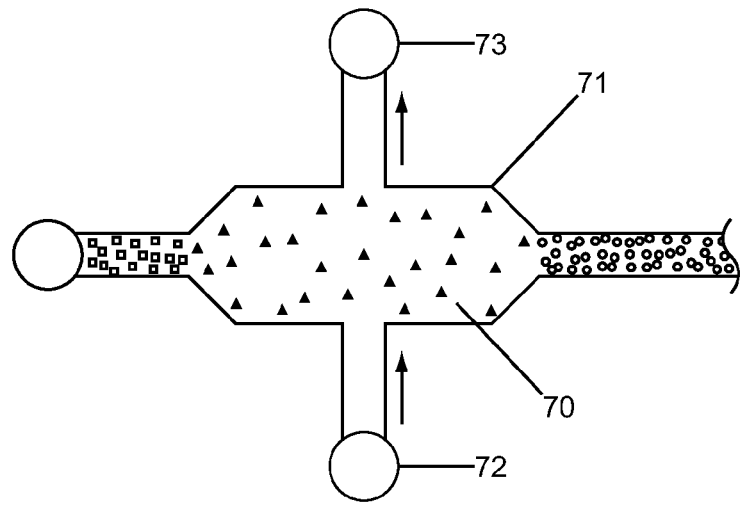
FIGS. 7A to 7C are schematic diagrams showing enhanced sample solution volume loading using a loading channel segment with a cross-section greater than the cross section of the stacking channel segment.
Figure 7B:
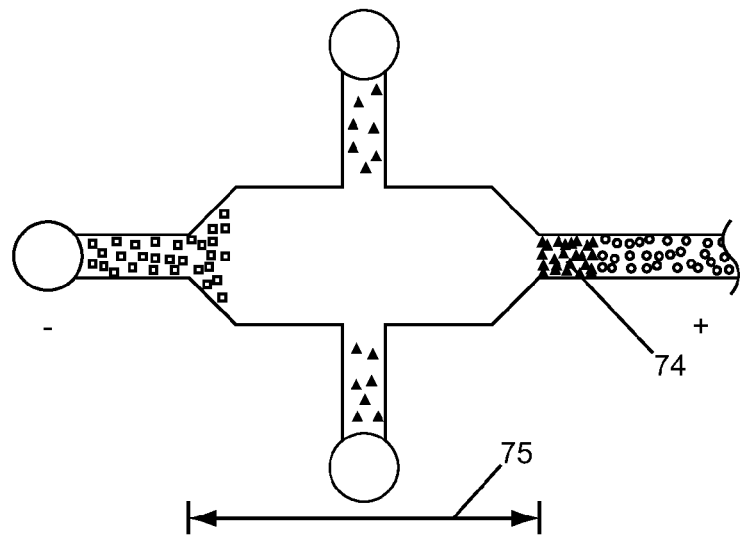
Figure 7C:
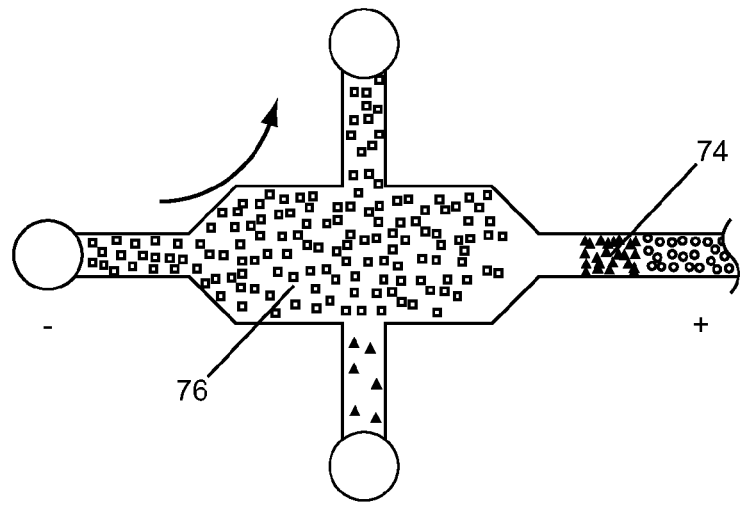

Optionally, a large volume of sample solution can be loaded into a loading channel segment having a cross-section greater than the cross-section of the stacking channel segment. As shown in FIG. 7A, sample solution 70 can be loaded into large cross-section loading channel segment 71, e.g., with a differential pressure across sample well 72 and waste well 73. Under the influence of an electric field, sample analytes 74 can be concentrated near the stacking channel segment entrance, as shown in FIG. 7B. Loading channel segments with increased cross section can concentrate analytes in a shorter time due to the reduced axial distance 75 for analyte travel as compared to a similar volume loading channel segment with a smaller cross section. Trailing electrolyte 76 can optionally be brought to a position adjacent to concentrated sample analytes 74 for subsequent ITP by, e.g., providing a pressure differential to flush the loading channel segment with trailing electrolyte, e.g., as shown in FIG. 7C.

Advantages can be obtained in methods of the invention by placing a spacer electrolyte between analyte sample segments for ITP. The spacer electrolyte can have a mobility intermediate between the trailing electrolyte and the leading electrolyte. The spacer electrolyte can have a mobility intermediate between two or more analytes of interest. The spacer electrolyte can provide, e.g., enhanced resolution between multiple analytes of interest. In one embodiment, spacer electrolyte can be present in loaded sample solutions to provide a spacer zone between analytes on application of an electric field. In another embodiment, spacer electrolyte can be loaded between cycles of multiple stacking. For example, multiple stacking can proceed as described above, but with spacer electrolyte present to the left of the initial stack, with spacer electrolyte present in one or more loaded sample solution segments, or by loading spacer electrolyte between cycles of loading sample solution segments. Spacer electrolytes can be adjusted as described above for adjustment of trailing and leading electrolyte mobilities to tailor spacer migration between analytes of interest.

Detecting Voltage Events

Detection of voltage events associated with, e.g., migration of solutions, analytes, and/or electrolytes in the stacking channel segment can provide, e.g., a consistent signal for initiation of stacked analyte application to a separation channel segment. During an ITP, voltage potentials across the stacking channel segment, or voltages measurable at any point along the stacking channel segment, can vary with time. From one ITP run to the next, there can be measurable voltage events that are consistent between runs and which can act as timing markers useful for consistent triggering of injections and the switch from an ITP to a different separation scheme.

Figures 8A, 8B, 8C, 8D:
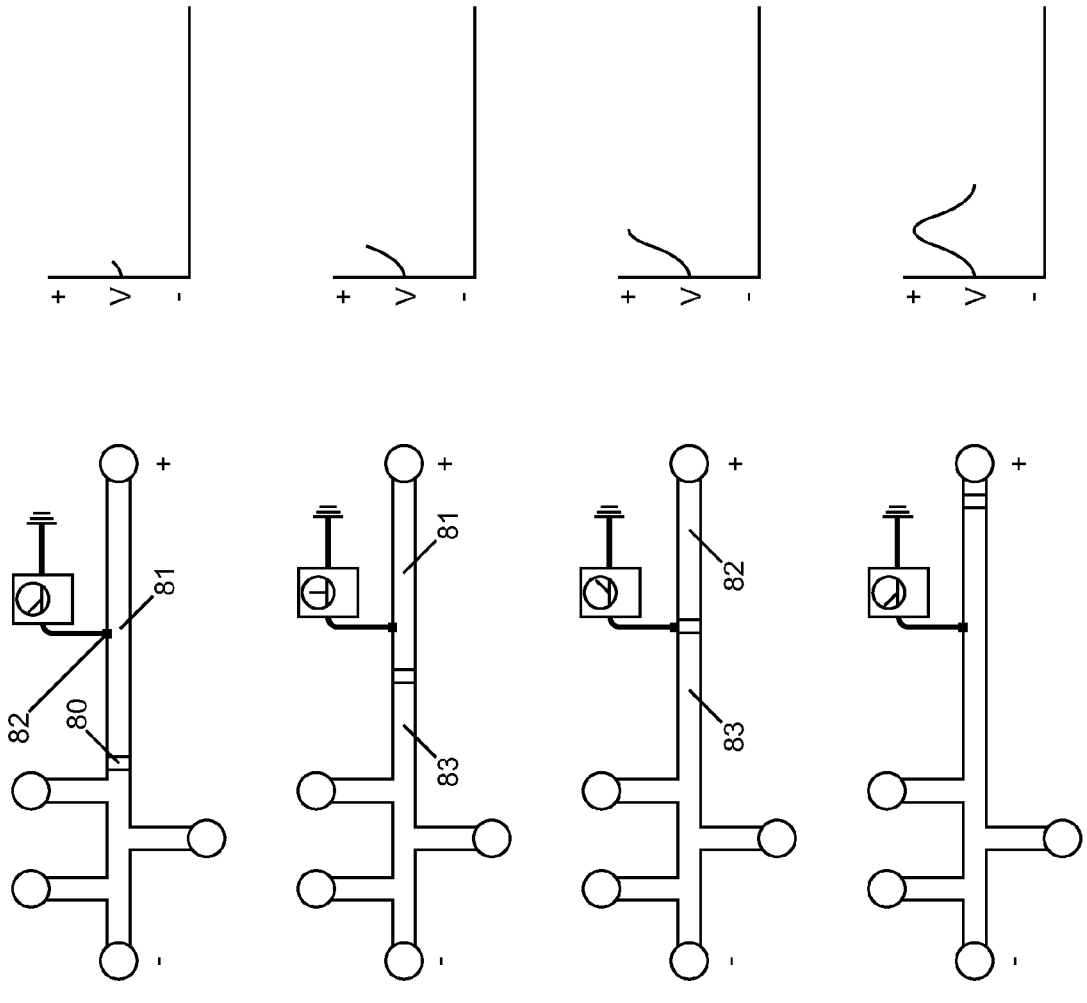
FIGS. 8A to 8D are schematic diagrams of voltage event detection at a contact point in a stacking channel segment.

In a typical embodiment of detecting a voltage event, trailing electrolyte, analyte, and leading electrolyte are flowing in a stacking channel segment during an ITP. The trailing electrolyte has a higher resistance to electric current flow than the leading electrolyte. With a voltmeter monitoring voltage, e.g., at a point half way along the stacking channel segment, as shown in FIG. 8, voltage events can be detected as the ITP proceeds. With sample solution 80 initially loaded and applied to the stacking column entrance, leading electrolyte 81 fills the stacking channel segment and the voltage detected at contact 82 half way along the channel segment is about half the ITP electric field voltage. As the analyte and trailing electrolyte 83 migrate down the stacking channel segment, resistance increases on the entrance side of the stacking channel segment resulting in a detectable voltage rise at the voltmeter contact, as shown in FIG. 8B. At about the time stacked analyte reaches the point of voltmeter contact, the difference in electrical resistance on the two sides of the point of contact reaches a maximum along with the detected voltage, as shown in FIG. 8C. Finally, as the analyte approaches the end of the stacking channel segment, now substantially filled with trailing electrolyte, the resistance on both sides of the contact equalize and detected voltage returns to about half the ITP electric field voltage, as shown in FIG. 8D. Voltage events, in this example could include the starting voltage value, the start of voltage rise, the rate of change (slope) of the voltage rise or fall, the maximum voltage (voltage peak), the slope of zero observed at maximum voltage, the return to starting voltage, any predetermined voltage, any relative voltage between locations in the channel segments, and/or the like. Consistent, but somewhat different, voltage profiles can be observed, e.g., with one or more voltmeter contacts located at different points along the stacking channel segment. These consistent measurable voltage events can be selected, e.g., to trigger switches in electric current or pressure differentials in channel segments to apply stacked analytes to a separation channel segment.

A separation channel segment in electrical contact with a stacking channel segment will have no substantial flow of electric current if the separation channel is not part of a complete circuit (e.g., a "dead end" with no ground connection) or if a float voltage is applied to the separation channel segment. In a preferred configuration for detecting voltage events, the voltmeter contact can be located at a point between the separation channel segment and the stacking channel segment, or at any location along the separation channel segment. In one preferred embodiment, voltage events can be detected by monitoring a separation channel segment float voltage.

Enhancing Separations in Skewing Channels

Separation of analytes of interest from other sample constituents can be enhanced by stacking the analyte during and/or after passage through a skewing channel segment. For example, sensitivity of an assay can be increased when sample constituents not of interest become dispersed by the turns while the analyte of interest continues to be focused by electrolytes in the isotachophoresis method.

Figure 9A:
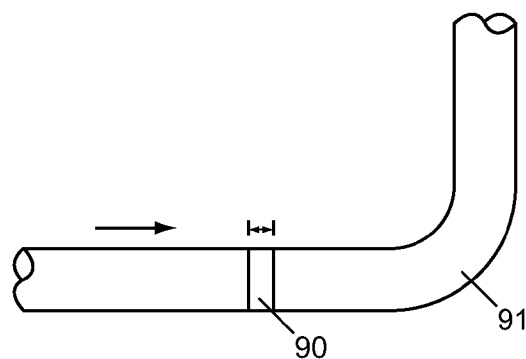
FIGS. 9A to 9D are schematic diagrams of analyte band skewing caused by flow through a skewing channel.
Figure 9B:
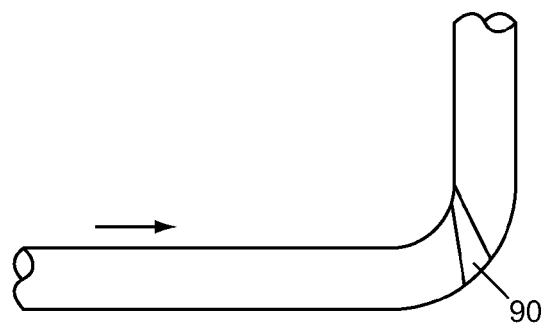
Figure 9C:
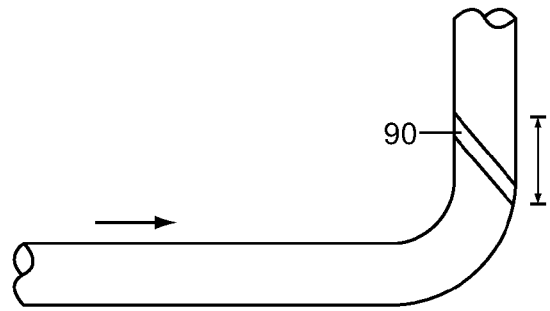
Figure 9D:
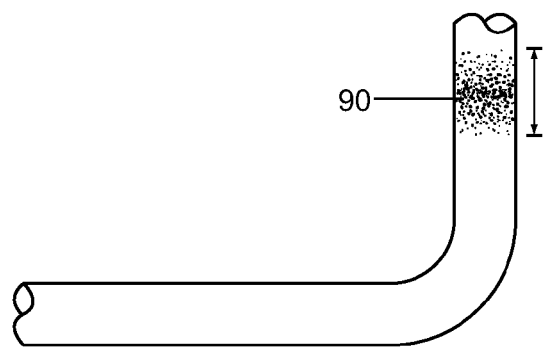

Analyte bands flowing in channels of an analytical system can become dispersed when the channel diverges from a straight path. For example, as shown in FIGS. 9A to 9D, analyte 90 flowing on the inside of turn 91 travels a shorter distance than analyte flowing on the outside of the turn. The initially compact band can become skewed and dispersed along a greater length of the channel, as shown in FIG. 9C. Axial diffusion of the skewed band can dilute the band and prevent realignment of the band, as shown in FIG. 9D. A detector focused on the band in FIG. 9A would detect a stronger and narrower maximum signal for the band than a detector focused on the band in FIG. 9D after skewing and diffusion. Such dispersion of bands can be problematic in many chromatographic analyses because of the resultant broadening and shortening of peaks. However, the present invention can combine, e.g., intentionally accentuated skewing with ITP technology to enhance separations by stacking analytes of interest while dispersing sample constituents not of interest.

Figure 10A:
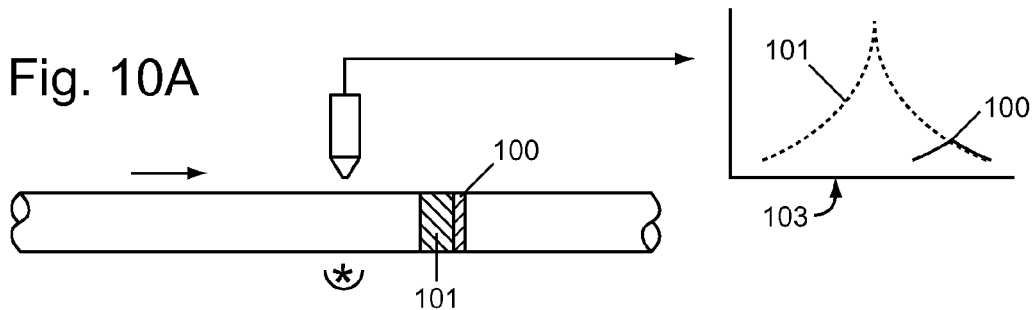
FIGS. 10A to 10E are schematic diagrams of sample constituent skewing and dispersion in skewing channel ITP while an analyte of interest band remains focused.
Figure 10B:
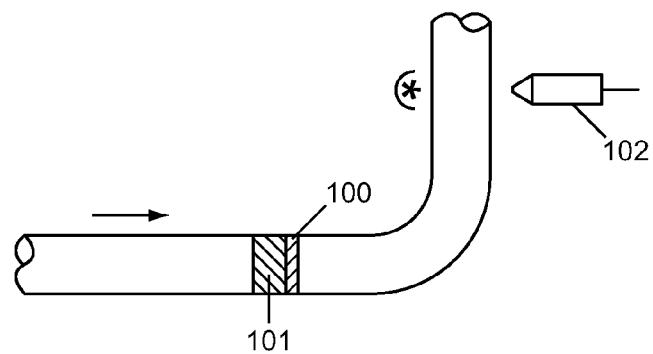
Figure 10C:
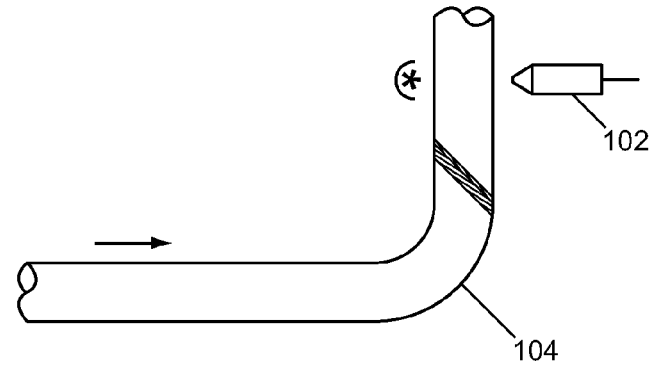
Figure 10D:
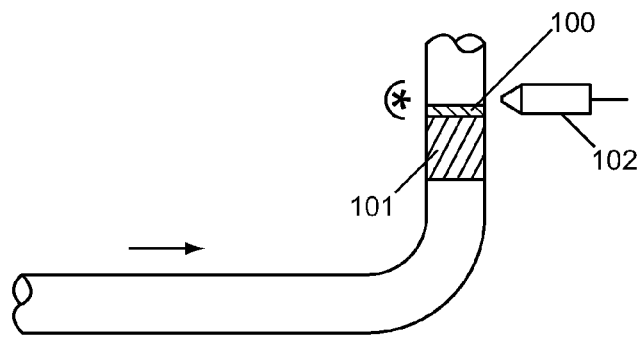
Figure 10E:
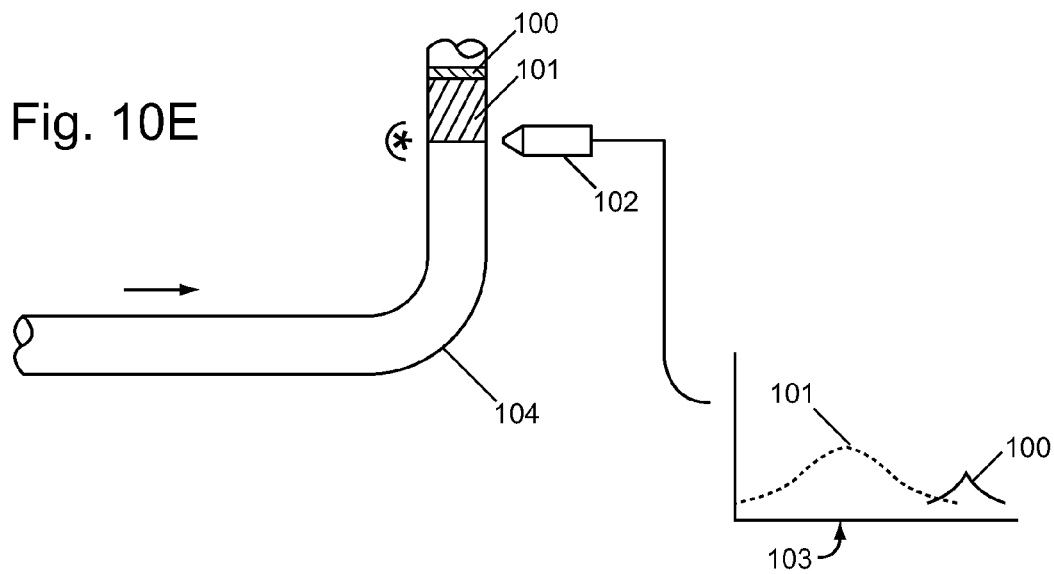

In one embodiment, for example, a small amount of analyte of interest can be separated from a larger amount of sample constituent not of interest with an enhanced degree of sensitivity and improved quantitation. In an ITP system without skewing channels, as shown schematically for example in FIG. 10A, a small amount of stacking analyte of interest 100 can migrate, e.g., between selected trailing and leading electrolytes, while a larger amount of sample constituent not of interest 101, with a mobility similar to the trailing electrolyte, migrates near the front of the trailing electrolyte. Detector 102 focused on the channel can fail to resolve the analyte and sample constituent peaks, as shown in detector output signal chart 103. The analyte sensitivity and quantitation capabilities can be enhanced by, e.g., introducing one of more skewing channel segments into the stacking channel. Analyte 100 and sample constituent 101 migrating in the staking channel (FIG. 10B) can become skewed and dispersed in skewing channel 104 (FIG. 10C). Sometime after exiting the skewing channel, the stacking forces of the leading and trailing electrolytes can focus and realign the analyte peak in the channel, while the unshepherded sample constituent peak remains skewed and becomes diffused. A detector focused on the channel can detect the presence and quantity of analyte against a diminished and less intrusive background of sample constituent.

The benefits of ITP separations in skewing channels can be increased by selecting trailing and/or leading electrolytes to enhance the stacking focus of the analyte while increasing the mobility difference between the electrolytes and the sample constituent. In selective ITP the mobilities of leading and trailing electrolytes are selected, e.g., to be near the known mobility of an analyte and/or to increase the difference in mobility between the electrolytes and one or more sample constituents not of interest. For example, in the situation described above, where the analyte of interest has a mobility greater than the sample constituent not of interest, the trailing electrolyte can be selected to have a mobility closer to the analyte than to the sample constituent so that, e.g., the analyte is closely shepherded while the sample constituent lags behind to experience the effects of skewing and diffusion. In a similar fashion, if the analyte of interest has a mobility less than the sample constituent not of interest, the mobility of the leading electrolyte can be selected to be between the analyte mobility and the sample constituent mobility to enhance skewing channel ITP separation. In a preferred embodiment, the mobility of an electrolyte is selected to be between the mobilities of the analyte of interest and one or more sample constituents not of interest but closer to the mobility of the analyte. In another example, both leading and trailing electrolytes can be selected to be close to the known mobility of the analyte of interest. This can provide particular benefits when both faster and slower sample constituents migrate near the analyte and/or when transient stacking prevails during the ITP.

The effectiveness of skewing channel ITP can vary widely depending on factors, such as, e.g., the radius of any turns involved, the internal diameter of the channel, the topography of the channel walls, the cross section of the skewing channel, the flow velocity, and the viscosity of solutions. For example, as is discussed in the Skewing Channel ITP Systems section below, skewing in a channel can be increased with short turn radii, repeated turns in the same direction, channel topographies that increase the difference between the surface length of opposite channel walls, and channel cross sections that are wider perpendicular to the axis of a turn. Appropriate conditions for a particular method or system can be derived, e.g., through calculation and/or experimentation.

To consider how diffusion can affect the amount of skew caused by a turn, a two-dimensional, nondimensionalized advection-diffusion equation can be considered (see also, Analytical Chemistry, vol 73, No. 6, 1350-1360, Mar. 15, 2001):

$$\frac{\partial c'}{\partial t'} + \underbrace{u'\frac{\partial c'}{\partial x'}}_{advection} = \frac{1}{Pe'_n}\left(\underbrace{\frac{w}{L}\left(\frac{\partial^2 r'}{\partial x'^2}\right)}_{\substack{axial \\ diffusion}} + \underbrace{\frac{L}{w}\left(\frac{\partial^2 r'}{\partial y'^2}\right)}_{\substack{transverse \\ diffusion}}\right)$$

wherein L is the length of the turning channel, w is the internal width of the turning channel, and $Pe'_w$, is the dispersion Peclet number; u', c', t', x' and y' are the normalized velocity, concentration, time, axial channel dimension, and transverse channel dimension, respectively. Three parameters, $Pe'_w$, L, and w, have been determined to be of special importance to skewing and dispersion of analytes under the influence of skewing channels in the present invention.

The Peclet number (Pe) is a dimensionless factor representing a ratio of advection (or forward movement) and diffusion of an analyte. If Pe is large, peaks skewed by passage through a first skewing channel can retain a stable oblique shape long enough to have it reversed by a second turn in the opposite direction. If Pe is small, peaks skewed in a skewing channel can diffuse across the width of the channel in a relatively short time to convert a skewed peak into a diffusely broadened peak. In methods of the invention, sample constituents not of interest can be most readily skewed and dispersed from analytes of interest, e.g., when conditions exist in skewing channels providing a Peclet number more than about the ratio of the length of the skewing channel over the internal width of the skewing channel (i.e., Pe>L/w). Significant benefits in skewing, diffusion, and dispersion of sample constituents not of interest in skewing channel ITP can be obtained where conditions provide a Peclet number more than about 0.01 times, 0.1 times, 1 time, 10 times, 100 times, or more, than the ratio of the skewing channel length over the skewing channel width.

Conditions affecting the Peclet number can be, e.g., conditions that influence advection and/or diffusion of molecules in the channels, as is known by those skilled in the art. For example, Pe can be influenced by the viscosity of solutions, the presence of a gel, temperature, molecular concentrations, the velocity of the molecule along the channel, the diameter of the channel, and/or the like. Adjustment of conditions controlling advection and diffusion can provide Peclet numbers, e.g., that result in desirable levels of sample constituent dispersion during and/or after passage through skewing channel segments of the invention.

Applying Stacked Analytes to Separation Channels

Analytes stacked by ITP can be injected into a separation channel segment, e.g., by applying an electric field or pressure differential across the separation channel segment and the stacked analytes. The field and/or pressure can cause migration or flow of analytes into the separation channel segment. Application of the field or pressure can be triggered by detection of a voltage event, as described above, to provide consistent and functional analyte injection timing. Application of the separation channel segment electric field or pressure differential can coincide with elimination of current flow in the stacking channel segment. The timing between the voltage event and the injection can be established to conform to particular configurations of channels, intersections, and solution segments. The timing can also play a key role in determining the peak resolution and signal strength as it can affect the amount of transient isotachophoresis that persists after the handoff.

Separation channel segments can provide conditions for electrophoretic separation of analytes and/or separation by selective media. In preferred embodiments, separation channel segments have a microscale dimension (e.g., a depth or width ranging from about 1000 μm to about 0.1 μm, or from about 100 μm to about 1 μm), e.g., to provide fast separations of small analyte sample volumes. Separation channel segments can have separation media, such as, e.g., a pH gradient, size selective media, ion exchange media, a viscosity enhancing media, hydrophobic media, and/or the like, capable of contributing to the resolution of analytes. Separation channel segments (as well as stacking channel segments) can have viscosity enhancing media, such as gels, to reduce electroosmotic flow (EOF) in separation modes where EOF is undesirable. Separation channel segments can be independent from other channel segments, or can share all or part of a channel with other channel segments, such as, e.g., loading channel segments and stacking channel segments. In a preferred embodiment, the separation channel segment is independent, but intersects in a fluid contact at some point along the length of the stacking channel segment.

Figure 11A:
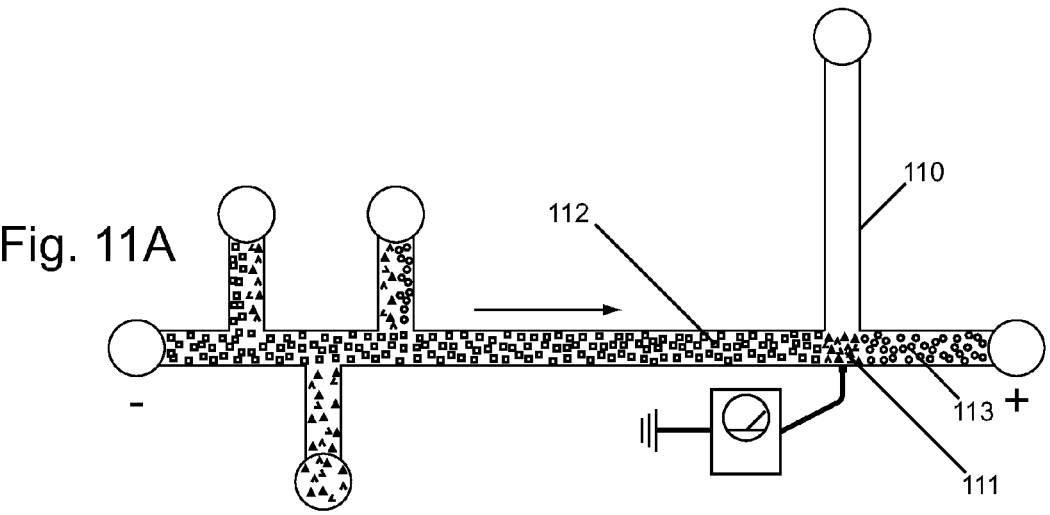
FIGS. 11A to 11C are schematic diagrams of stacked analyte application to a separation channel segment.
Figure 11B:
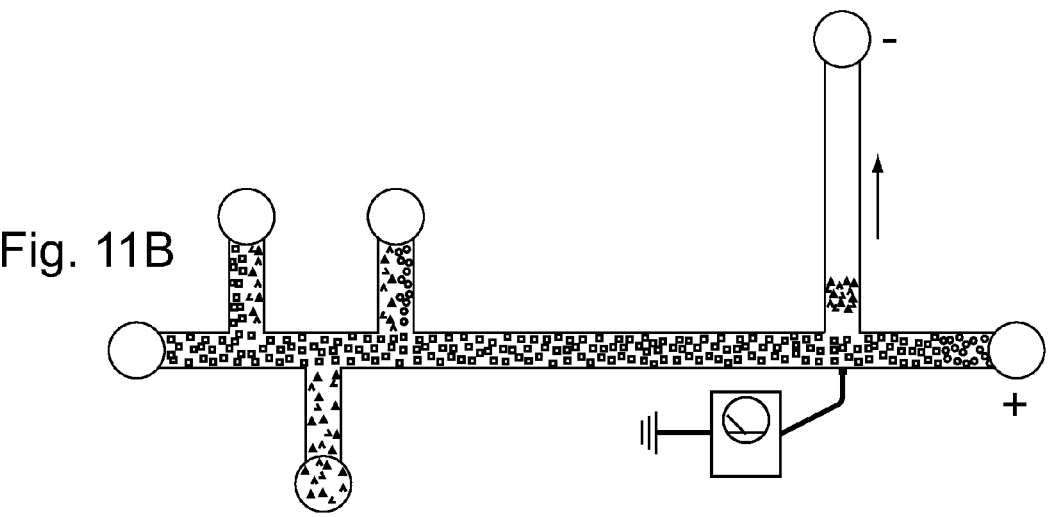
Figure 11C:
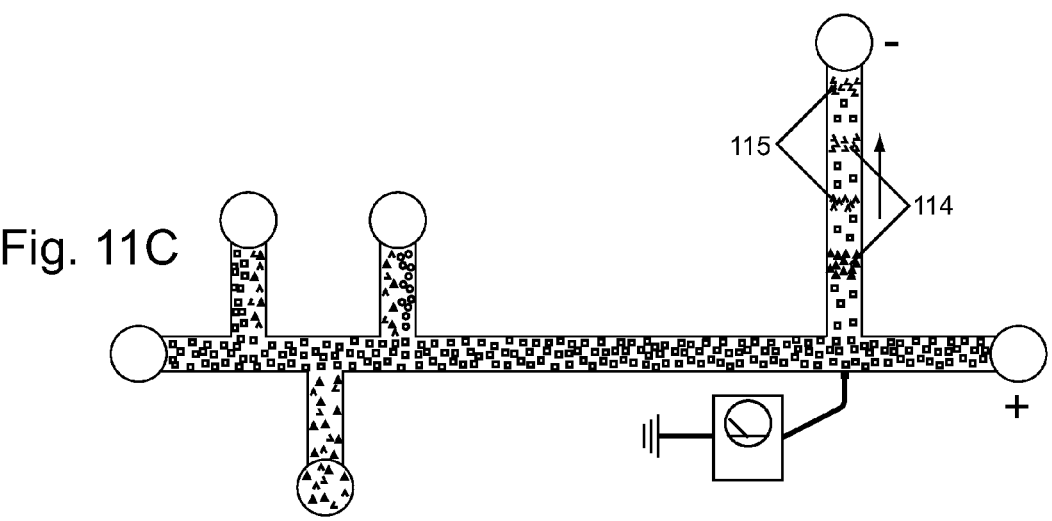

In a typical embodiment, stacked analyte from an ITP separation is injected into a separation channel segment when a peak voltage is detected at the intersection of a stacking channel segment and the separation channel segment. For example, the float voltage in separation channel segment 110 reaches a maximum (and the rate of voltage change, or slope of the voltage profile, becomes zero) as stacked analytes 111, sandwiched between trailing electrolyte 112 and leading electrolyte 113, migrate in an ITP past a voltmeter contact at the intersection of the separation channel segment with the stacking channel segment, as shown in FIG. 11A. The voltage maximum can trigger the elimination of the ITP electric field in the stacking channel segment and the application of an electrophoresis electric field in the separation channel segment to induce migration (application) of stacked analytes 111 into the separation channel segment, as shown in FIG. 11B. Migration of analytes through selective media of the separation channel segment can separate (resolve) analytes of interest 114 from sample constituents not of interest 115 that co-migrated with the analytes through the stacking channel segment during ITP, as shown in FIG. 11C. In some embodiments, multiple analytes of interest that stacked together, or in proximity to each other, during ITP can be resolved from each other in the separation channel segment, e.g., by capillary zone electrophoresis.

Alternate schemes for timing of injection will be appreciated by those skilled in the art. Such alternate schemes can be based, e.g., on calculations or models, or can be determined empirically. For example, time delays can be built into triggered responses based on channel volumes, channel geometry, voltmeter contact location, choice of voltage events, the location of analytes relative to solution features affecting voltage events, and/or the like. In a particular example, wherein analyte is stacked near a trailing electrolyte interface in a transient ITP (not yet reaching a steady state) and the remaining sample solution bolus has a high electrical resistance, a suitable trigger time can be a certain time after the voltage peak to allow the stacked analyte additional migration time to reach the intersection with the separation channel segment.

Application of an electric field along the separation channel segment can be automatic (that is, not requiring manual switching). Such automatic application of the electric field can be accomplished, e.g., by electronic devices and algorithms known in the art. For example, a voltmeter can be set to trip a switch when voltage at a contact reaches a set level. In preferred embodiments, a logic device, such as, e.g., an integrated circuit or a computer, can be programmed to initiate switching of actuators according to preset parameters (e.g., the occurrence of defined voltage events).

Detecting Analytes

Analytes separated in by methods of the invention can be detected in the separation channel segment and/or sequentially after elution from the separation channel segment. Appropriate detectors can, e.g., be fixed to monitor analytes in a detection channel, sequentially scan for analytes in channel segments, or provide continuous imaging of entire channels.

Appropriate detectors are often determined by the type of analyte to be detected. Proteins and nucleic acids, for example, can often be detected by spectrophotometric monitoring of particular light absorption wavelengths. Many ionic analytes of interest can be detected by monitoring changes in solution conductivity. Many analytes are fluorescent or can be labeled with fluorescent markers for detection using a fluorometer. Many analytes in solution, particularly carbohydrates, can be detected by refractometry.

In a typical embodiment, detecting can be by monitoring transmission of a light source through a separation channel segment using a photomultiplier tube (PMT) focused on the channel with a microscope lens. Those skilled in the art will appreciate how such an arrangement can be configured as a fluorescence detector by addition of an appropriate excitation light source, such as, e.g., a laser or filtered light from a lamp. Optionally, the lens can be mounted on an X-Y scanning mechanism to monitor any location on a microfluidic chip. With such an arrangement, the length of a separation channel segment can be scanned for analytes, e.g., resolved along a pH gradient. In another embodiment, conductivity meter sensors can be mounted across a separation channel outlet to monitor charged analytes as they elute from the channel segment.

Detectors can be in communication with data storage devices and/or logic devices to document assay runs. Analog output from detectors, such as PMTs and conductivity meters, can be fed to chart plotters to retain a trace of the analyte separation profile on paper. Analog to digital converters can communicate detection signals to logic devices for data storage, separation profile presentation, and/or assay evaluation. Digital logic devices can greatly facilitate quantitation of analytes by comparison to appropriate standard curves from regression analysis.

Analyte Injection Systems

Electrokinetic analyte injection systems described herein can provide sensitive analyte detection with high resolution in a highly consistent manner. Analytes selectively stacked in a stacking channel segment can be injected (applied) into a separation channel segment with precise timing based on detection of voltage events in the channels. Such precision can be enhanced by provision of automated injection subsystems.

Systems of the invention generally include, e.g., an analyte stacking in a channel, a voltage detector in communication with a controller and in contact with the channel at one or more locations, an electric current or pressure differential established in the channel when a selected voltage event is detected by the voltage detector and communicated to the controller. The channel can include stacking channel segments and separation channel segments that intersect, form a continuous channel or which share common channel sections. Analytes applied to the separation channel segment and separated can be, e.g., detected by a detector in communication with a logic device to determine the presence of particular analytes or to evaluate the quantity of analytes.

Channels

The channel of the invention can be, e.g., a single multifunction channel comprising loading segments, stacking segments, separation segments, and/or detection segments. Optionally, the channel can include separate loading channel segments, stacking channel segments, and separation channel segments in fluid contact at intersections. In a preferred embodiment, as shown schematically in FIG. 11, the loading channel segment is an extension of the stacking channel segment, and the separation channel segment is in fluid contact with the stacking channel segment through an intersection where analyte injection takes place. Channels of the systems can be any known in the art, such as, e.g., tubes, columns, capillaries, microfluidic channels, and/or the like. In a preferred embodiment, the channels are microscale channels, e.g., on a microfluidic chip.

Channels of a microfluidic device can be embedded on the surface of a substrate by mold injection, photolithography, etching, laser ablation, and the like. The channels can have a microscale dimension, such as, e.g., a depth or width ranging from about 1000 µm to about 0.1 µm, or from about 100 µm to about 1 µm. Fluids can flow in the channels, e.g., by electroosmotic flow, capillary action (surface tension), pressure differentials, gravity, and/or the like. Channels can terminate, e.g., in wells of solutions and/or at intersections with other channels or chambers. Channels can have electrical contacts, e.g., at each end to provide electric fields and/or electric currents to separate analytes or to induce EOF. Detectors can be functionally associated with channels to monitor parameters of interest, such as, e.g., voltages, conductivity, resistance, capacitance, electric currents, refractivity, light absorbance, fluorescence, pressures, flow rates, and/or the like. Microfluidic chips can have functional information communication connections and utility connections to supporting instrumentation, such as electric power connections, vacuum sources, pneumatic pressure sources, hydraulic pressure sources, analog and digital communication lines, optic fibers, etc.

Figure 12A:
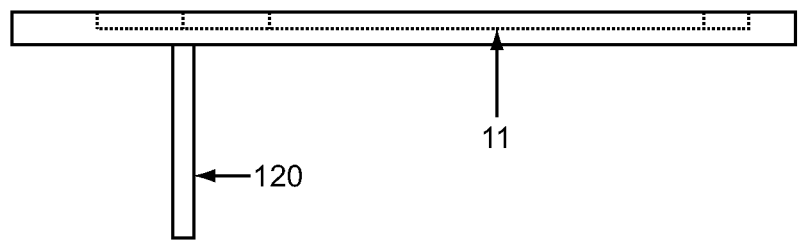
FIGS. 12A and 12B are schematic diagrams of a microfluidic chip with a collector tube feeding sample solutions to a loading channel segment.
Figure 12B:
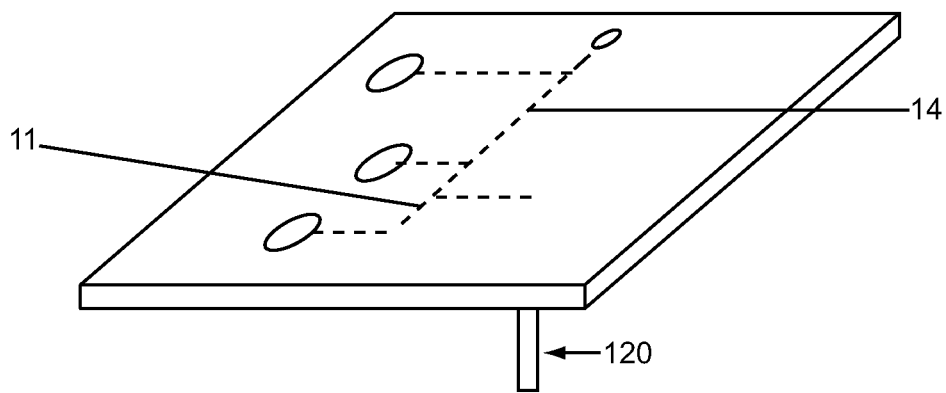

The channel can include, e.g., a load channel segment to introduce one or more sample solution volumes into the channel. Such loading channels can be configured in ways appreciated by those skilled in the art, such as, e.g., as an injector loop, to include an a collector tube 120 to a microfluidic chip, as shown in FIG. 12, and/or as a flushed channel segment, as shown schematically in FIGS. 5A to 5C. Loading channel segments can have a cross-section greater than the cross-section of the stacking channel segment, as shown in FIG. 7, to provide rapid concentration of analytes near the stacking channel segment entrance from a large volume of sample solution.

Channels of the systems can contain gelatinous substances to beneficially affect migration and flow characteristics of the channels. Gels can be incorporated into channels to reduce unwanted electroosmotic flows of solutions while providing a more electrophoretic character to a separation. Gels can influence the relative migration rates of analytes and/or electrolytes by slowing the progress of larger molecules. Gels can provide tools to help adjust migration zones for analytes and ITP electrolytes in stacking channel segments. For example, analytes of interest are generally larger than commonly used ITP electrolytes. By placing a gel in a stacking channel segment, a fast analyte (large but with a high charge to mass ratio) can be slowed to migrate behind a leading electrolyte small molecule salt or buffer. Optionally, a gel can slow an analyte to migrate only marginally faster than a trailing electrolyte. Gel resistance to large molecule migration can be adjustable, e.g., by altering the type of gel, concentration of gel matrix, and the extent of gel matrix cross-linking. Gels can provide enhanced concentration and/or resolution to analytes in stacking or separation channel segments. One or more different gels can be present in either the stacking channel segment or the separation channel segment.

Stacking channel segments can function to selectively stack analytes of interest, e.g., by ITP, for injection into a separation channel segment for further resolution and detection. Stacking channel segments can have electrical contacts, e.g., at each end, for application of electric fields suitable for analyte stacking. Stacking channel segments can have fluid contacts with, e.g., externally driven pneumatic or hydraulic manifolds so that pressure driven flows, such as electrolyte loading or the pull back for the multiple stacking technique discussed in the "Stacking Analytes of Interest" section above, can be practiced. Stacking channel segments can contain, e.g., electrolytes, such as trailing electrolytes, spacer electrolytes, and/or leading electrolytes, suitable for isotachophoresis (ITP), as discussed in the Methods section above. The stacking channel segment can have trailing electrolyte well 18, as shown in FIG. 1, and leading electrolyte well 19, for introduction of electrolytes into channel segments.

Figure 13A:
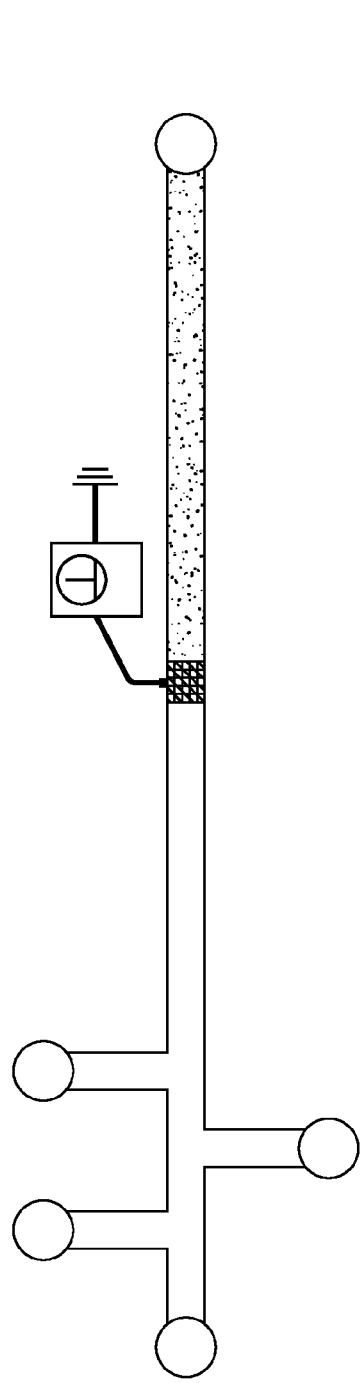
FIGS. 13A and 13B are schematic diagrams of an analyte injection system wherein a stacking channel segment shares a common channel with a separation channel segment.
Figure 13B:
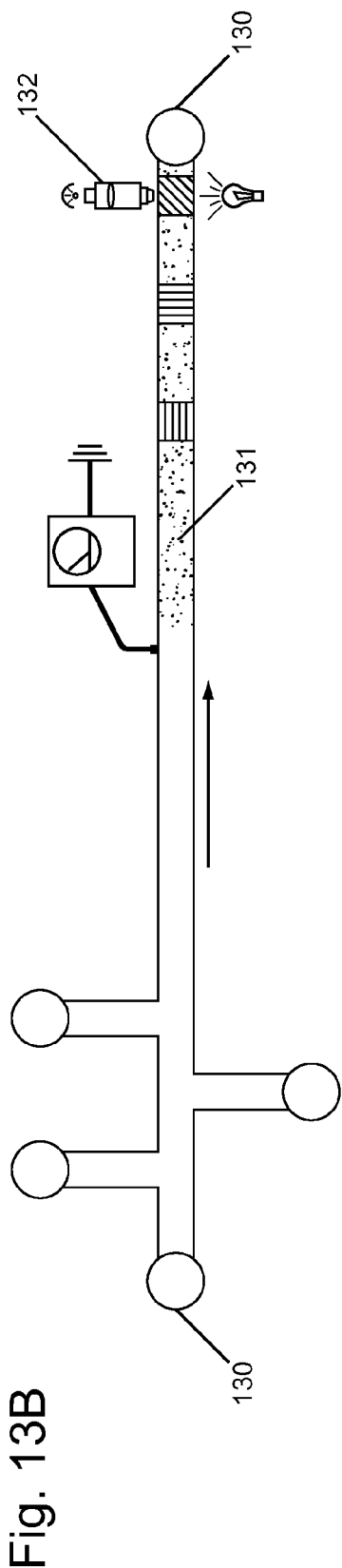

Separation channel segments can receive stacked analytes by injection from stacking channel segments for further resolution by separation techniques, such as, e.g., additional rounds of ITP, ion exchange, size exclusion, hydrophobic interaction, reverse phase chromatography, isoelectric focusing, capillary zone electrophoresis, and/or the like. Separation channel segments can include electric contacts for application of electric fields along the channel segment and/or external connections with pressure sources to drive fluid flows. Separation channel segments can be, e.g., a channel segment intersecting a stacking channel segment, a channel segment continuing a common channel with a stacking channel segment, and/or a channel segment functionally sharing channel sections with a stacking channel segment. In a typical embodiment, the separation channel segment intersects the stacking channel segment at some point along the stacking channel segment length, as shown in FIG. 11. In this embodiment, sample constituents not of interest can remain in separate stacking channel segment sections after injection of stacked analytes of interest into the separation channel segment. In other embodiments, e.g., the stacking and separation channel segments can functionally reside in a common channel without an intervening intersection. For example, e.g., as shown in FIG. 13A, stacking can continue in a channel segment until a voltage event is detected. On detection of the voltage event, conditions can change in the channel for a transition to a separation mode. Such a transition can include, e.g., application of a differential pressure between channel ends 130 to induce analyte flow into size exclusion resin 131, as shown in FIG. 13B. Smaller molecules will elute past detector 132 before larger molecules. Other examples of transitions to separation modes can include, e.g., changes in the direction of electric current flow, changes in the direction of fluid flow, injections of separation buffers into a channel, changes in an electric field voltage, and/or the like.

Skewing Channel ITP Systems

Isotachophoresis systems of the invention can include skewing channel segments in, and/or before, the stacking channel to enhance the separation of analytes of interest from sample constituents not of interest. The sample constituents can be dispersed while the analyte of interest is focused by stacking, e.g., in the skewing channels. The separation enhancement can be promoted, e.g., by turning through cumulatively large angles, sharp turning, skewing channel cross sections having relatively large widths, skewing channel topographies with opposite surfaces of different length, and/or skewing channel systems having conditions providing a Peclet number more than about the ratio of the skewing channel length over the skewing channel width.

Figure 14A:
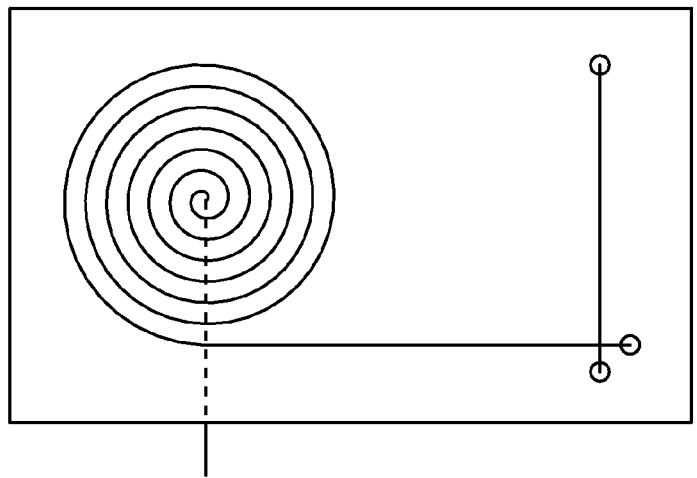
FIGS. 14A to 14C are schematic diagrams of an analyte injection system incorporating skewing channels in spiral and serpentine configurations.
Figure 14B:
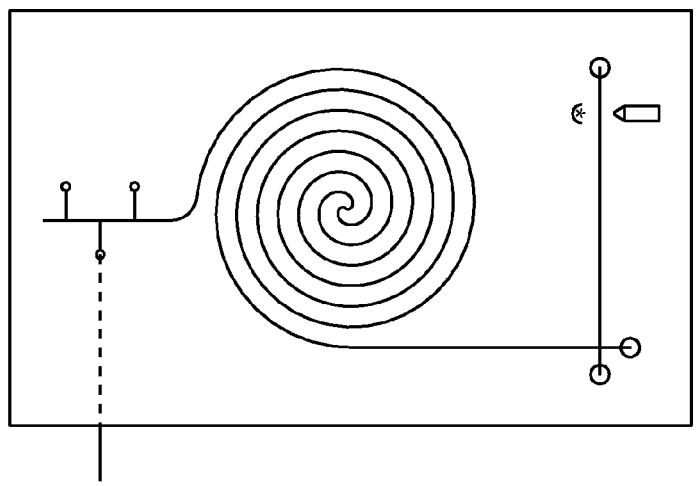
Figure 14C:
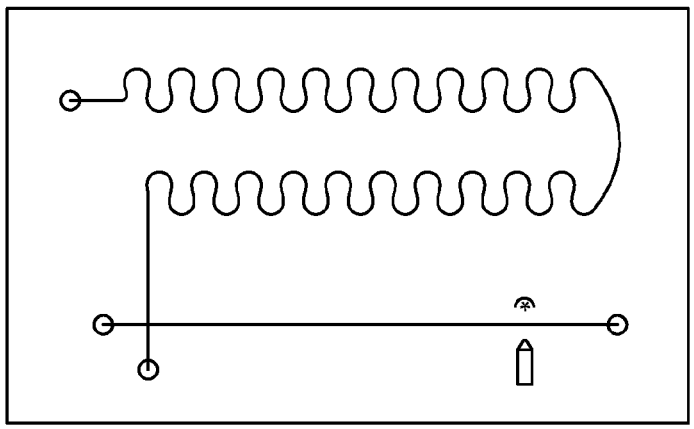

One way to increase skew and dispersion in skewing channel segments is to provide greater turning angles in the channel. In a two dimensional plane, turning angles can be accumulated, e.g., with continuous spiral turns or switching serpentine turns as shown in FIGS. 14A to 14 C. Spiral turns have the advantage that turning angles can accumulate through a large number of degrees in one direction, with a concomitant accumulation of skew. A disadvantage of spiral skewing channels can be the inherent continuous expansion of the turn radius into a range of less effective curvatures. Spiral skewing channel configurations can also entail difficult access problems for connections to the inner channel end. One way to provide accessible channel ends in a spiral skewing channel configuration can be to have side by side spiraling channels running in and out of the center, as shown in FIG. 14B. Alternately, the access to a spiral channel end can be provided in the third dimension, e.g., through a sipper tube or a back channel in another plane, e.g., as shown in FIG. 14A. Another limitation on the length of the spiral channel is that the Peclet number required for optimal skewing increases as the length of the spiral channel increases. Serpentine skewing channels, as shown in FIG. 14C, can provide easy access to channel ends but complimentary turns can cancel the skew of previous turns, particularly where the Peclet number is large or the time is short between turns. Optionally, three dimensional skewing channels can be employed, such as helices and coils.

Skew and dispersion from passage through skewing channel segments can be more pronounced in channels that make sharp turns relative to the internal channel diameter. For example, skew is increased for skewing channels with a high ratio of channel internal diameter over turn width. In one embodiment, the skew from a skewing channel segment having turns is increased when the cross-section of the channel is greater along the radius of the turn (skewing channel internal width) than perpendicular to the turn radius (skewing channel depth).

Figure 15A:
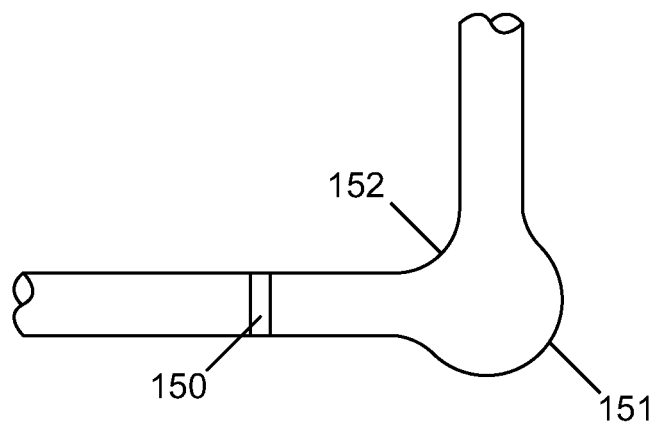
FIGS. 15A to 15C are schematic diagrams of a skewing channel with an increased ratio of outside travel distance over inside travel distance through a turn.
Figure 15B:
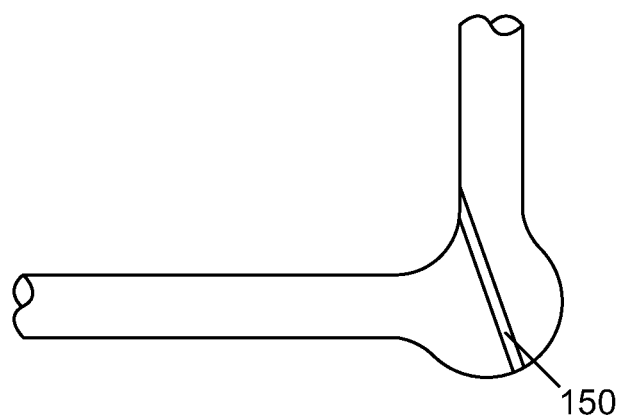
Figure 15C:
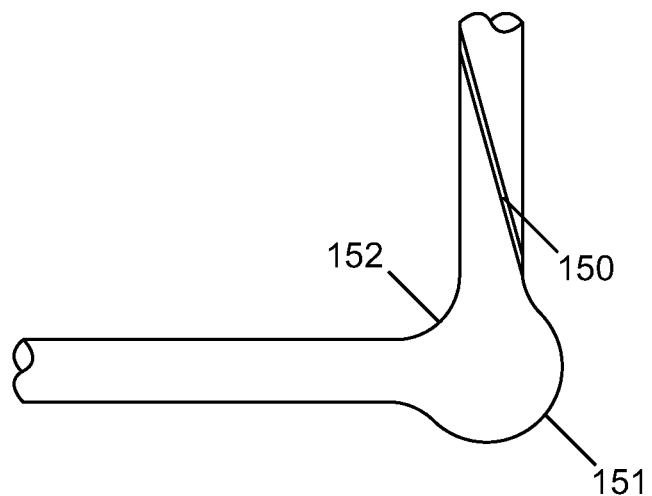
Figure 16A:
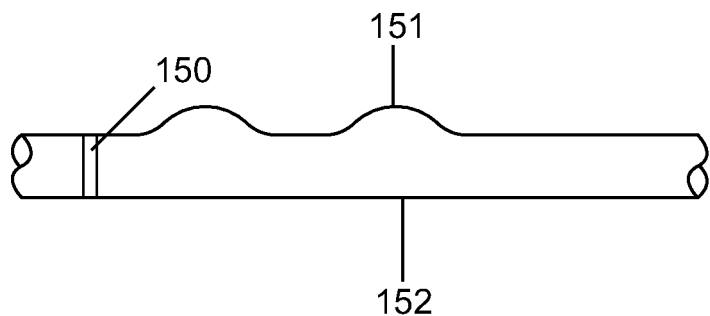
FIGS. 16A to 16C are schematic diagrams of a skewing channel with skewing provided by providing a travel surface distance on one side greater than for the other side of the channel.
Figure 16B:
Figure 16C:

The topography of a skewing channel segment can affect the skew and dispersion of migrating analytes. For example, channel surface contours that increase the ratio between the travel distance along the outside of a turn over the travel distance along the inside of the turn can increase skew. Skew can be increased by increasing channel internal width relative to channel depth at turn points. As shown in FIG. 15, analyte 150 can become highly skewed by flowing through a turn having a bolbus outer turn surface. Skew can be enhanced in skewing channels where the travel surface distance on a first side 151 of the skewing channel is greater than the travel surface distance on a second side 152 of the skewing channel, even if there is no curvature in the skewing channel overall, as shown in FIG. 16. For example, significant skewing can be provided from differences in opposite surface travel distances ranging from more than about 500%, to 100%, to 50%, to 10%, or less.

Selective stacking of the analyte of interest between leading and trailing electrolytes is an important aspect of skewing channel ITP systems of the invention. Analytes of interest can be continuously refocused between the electrolytes during and/or after skewing while sample constituents not of interest become dispersed. The mobility of an analyte of interest can be known from calculations or by empirical data. The trailing and/or leading electrolyte can be selected to have a mobility between those of the analyte of interest and intrusive sample constituents not of interest. To enhance focusing of the analyte and dispersion of sample constituents, the electrolytes can be selected to have mobilities closer to that of the analyte of interest than the sample constituents.

Skewing ITP channel segments can be incorporated into the systems and methods of injecting analytes described above. An analyte of interest can be injected into a separation channel at higher purity after dispersion of other sample constituents by skewing channel ITP. Injection of the analyte can be initiated on detection of a voltage event.

Voltage Detectors

Voltage detectors in systems of the invention can be in contact with channels to detect voltage events communicated to a controller. The type and complexity of voltage detectors can depend on, e.g., channel hardware configurations and the type of voltage event to be detected.

Voltage detectors can range from, e.g., simple relay switches tripped by a voltage, to analog galvanometers, to analog devices with chart recorders, to voltmeters with digital outputs for evaluation by logic devices. Voltmeters generally detect a voltage potential between electrodes at two locations, such as, e.g., a contact location in a channel and a ground, or between two different locations in a channel. The location of the voltage electrode contacts with the channel can change the voltage profile detected during a stacking run. However, a well defined voltage event can often be determined for consistent and unambiguous triggering of an injection for voltmeter contacts at a wide range of channel locations (e.g., the voltmeter contact does not have to be at an intersection between stacking and separation channel segments).

In one embodiment, voltmeter contacts can be located at two ends of the channel. As trailing electrolyte, of relatively high resistance, displaces leading electrolyte in the channel, the voltage required to maintain a selected current through the channel can increase. A voltage event to trigger injection in this case can be, e.g., a preset voltage.

In another embodiment, voltmeter contacts can be located at a ground (or other voltage reference) and at any point in a separation channel segment intersecting a stacking channel segment. If electric current is not allowed to flow through the separation channel segment (e.g., where the separation channel segment is held at zero current by a float voltage, or where the separation channel segment not part of a complete circuit), any location in the separation channel segment will reflect the stacking channel segment voltage at the intersection. Voltage detected in the separation channel segment can rise to a peak and fall as the TE/LE interface passes the intersection, in a fashion similar to the voltage profile of FIG. 8, as will be appreciated by those skilled in the art.

Where voltage is being monitored in a separation channel segment without electrical current and in contact with the stacking channel segment, the lack of current can be by, e.g., float voltage regulation or circuit isolation. A float voltage regulator device can be an electronic device, known in the art, that detects electric current flow in a channel segment and applies a voltage to the channel segment that neutralizes any voltage potential across the channel segment, thus preventing a flow of electric current. A float voltage regulator can optionally be configured to adjust a channel segment voltage differential to provide a selected constant current in the channel segment. Another way to prevent electric current flow in a channel segment is to ensure that the channel segment is not a part of a completed electric circuit. For example, an electric switch can be present at one end of the channel segment to selectively open or close any associated electric circuits.

The voltmeter can communicate with a controller for initiation of analyte application (injection) to a separation channel segment. Initiation of injection can be manual or automatic. For example, the voltmeter can provide a visible voltage readout for a system operator (the controller) to manually switch channel electric fields or fluid flows on observation of a voltage event, such as a selected voltage or voltage peak. In another example, the controller is a digital logic device in electronic communication with the voltmeter and set to automatically apply stacked analytes to a separation channel segment on detection of a selected voltage event.

Analyte Detectors

Appropriate analyte detectors can be incorporated into systems of the invention to detect analytes. The type and configuration of detectors can depend, e.g., on the type of analyte to be detected and/or on the layout of channels. Analyte detectors can be in communication with logic devices for storage of analyte detection profiles and evaluation of analytical results.

Analytes for detection in the systems can range widely, with many being charged molecules or molecules modified to have a charge. For example, analytes of interest can be proteins, nucleic acids, carbohydrates, glycoproteins, ions, and/or the like. Although stacking can take place by alternate mechanisms, such as size exclusion, stacking is driven by migration of charged analytes in an electric field for many systems of the invention. It will be appreciated by those skilled in the art that non charged analytes of interest can receive a charge for electrophoretic stacking by appropriate adjustment of pH or derivatization of the analyte with a charged chemical group.

Analyte detectors in the systems can be any suitable detectors known in the art. For example, the detectors can be fluorometers, spectrophotometers, refractometers, conductivity meters, and/or the like. Analytes not detectable by available detectors can often be derivatized with a marker molecule to render then detectable. The detectors can be mounted or focused to monitor analytes in the channel segments, including, e.g., intersections and/or separation channel segments. Detectors can monitor analytes as they exit separation channel segments, e.g., in detection channels of chambers.

Analyte detectors can monitor a channel location, sequentially scan a channel length, or provide a continuous image of separated analytes. In one embodiment, a stationary spectrophotometric detector can be a photomultiplier tube focused on a particular channel location or intersection. In another embodiment, the analyte detector can be a fluorometer focused on microchannels through a confocal microscope lens mounted to an X-Y transporter mechanism to sequentially scan analytes separated in channels of a microfluidic device. In another embodiment, the analyte detector can be a charge coupled device (CCD) array capable of providing an image of numerous separations in multiple separation chambers at once.

The analyte detector can be in communication with a logic device for storage and evaluation of analytical results. Logic devices of the systems can include, e.g., chart recorders, transistors, circuit boards, integrated circuits, central processing units, computer monitors, computer systems, computer networks, and/or the like. Computer systems can include, e.g., digital computer hardware with data sets and instruction sets entered into a software system. The computer can be in communication with the detector for evaluation of the presence, identity, quantity, and/or location of an analyte. The computer can be, e.g., a PC (Intel x86 or Pentium chip—compatible with DOS®, OS2®, WINDOWS® operating systems) a MACINTOSH®, Power PC, or SUN® work station (compatible with a LINUX or UNIX operating system) or other commercially available computer which is known to one of skill. Software for interpretation of sensor signals or to monitor detection signals is available, or can easily be constructed by one of skill using a standard programming language such as Visualbasic, Fortran, Basic, Java, or the like. A computer logic system can, e.g., receive input from system operators designating sample identifications and initiating analysis, command robotic systems to transfer the samples to the loading channel segments of the system, control fluid handling systems, control detector monitoring, receive detector signals, prepare regression curves from standard sample results, determine analyte quantity, and/or store analytical results.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, many of the techniques and apparatus described above can be used in various combinations.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of separating an analyte of interest from one or more sample constituents not of interest, the method comprising:
    stacking the analyte of interest between a first end and a second end of a first channel by isotachophoresis, the first channel further comprising a skewing channel segment between the first end and the second end;
    skewing the analyte and the one or more sample constituents not of interest by flowing the analyte and the one or more sample constituents not of interest through the skewing channel segment toward the second end;
    stacking the skewed analyte one or both of while within and after exiting the skewing channel segment to form a focused analyte band; and
    producing and maintaining axial diffusion of the skewed one or more sample constituents not of interest.

2. The method of claim 1, wherein the analyte comprises one or more of a protein, a nucleic acid, a carbohydrate, a glycoprotein, a derivatized molecule, and an ion.

3. The method of claim 1, wherein the first channel comprises a trailing electrolyte and a leading electrolyte, which electrolytes comprise different mobilities, and wherein the trailing electrolyte and the leading electrolyte differ in one or more of a pH, a viscosity, a conductivity, a size exclusion, an ionic strength, an ion composition, and a temperature.

4. The method of claim 1, wherein the isotachophoresis comprises selective isotachophoresis.

5. The method of claim 1, wherein the skewing channel segment comprises a serpentine curve.

6. The method of claim 1, wherein the skewing channel segment comprises a helix.

7. The method of claim 1, wherein the skewing channel segment comprises an angle.

8. The method of claim 1, wherein the skewing channel segment comprises a coil.

9. The method of claim 1, wherein the skewing channel segment comprises a spiral.

10. The method of claim 1, wherein the skewing channel segment comprises conditions providing a dispersion Peclet number more than the ratio of the skewing channel length over the skewing channel width.

11. The method of claim 1, wherein the skewing channel segment comprises conditions providing a dispersion Peclet number more than 0.1 times a ratio of the skewing channel length over the skewing channel width.

12. The method of claim 1, wherein the first channel has a greater internal width at the skewing channel segment.

13. The method of claim 1, wherein an internal width of the skewing channel segment is greater than an internal depth of the skewing channel segment.

14. The method of claim 1, wherein a travel surface distance on a first side of the skewing channel segment is greater than a travel surface distance on a second side of the skewing channel segment.

15. The method of claim 14, wherein the difference between the travel surface distances of the first side and the second side is at least about 25%.

16. The method of claim 1, further comprising:
    detecting a voltage potential in the first channel; and
    applying an electric field or a pressure differential along a first channel segment when a selected voltage event is detected, thereby applying the stacked analytes to a second channel.

17. The method of claim 16, wherein the second channel comprises a separation channel.

18. The method of claim 16, wherein said applying an electric field comprises switching from a substantial lack of current in the second channel and a current in the first channel to a current in the second channel and a substantial lack of current in the first channel.

19. The method of claim 16, wherein said applying an electric field or pressure differential along the channel segment is automatic when the voltage event is detected.

20. The method of claim 16, further comprising detecting the analyte in the second channel or detecting the analyte eluting from the second channel.

21. A method of separating an analyte of interest from one or more sample constituents not of interest, the method comprising:
    stacking the analyte of interest and the one or more sample constituents not of interest to form a compact analyte band and a compact constituents not of interest band;
    skewing the compact analyte band to form a skewed analyte band and skewing the compact constituents not of interest band to form a skewed constituents not of interest band; and
    stacking the skewed analyte band and the skewed constituents not of interest band to form a focused analyte band separate from an axially dispersed constituents not of interest band.

* * * * *